United States Patent [19]

Hogan et al.

[11] Patent Number: 5,176,996

[45] Date of Patent: Jan. 5, 1993

[54] METHOD FOR MAKING SYNTHETIC OLIGONUCLEOTIDES WHICH BIND SPECIFICALLY TO TARGET SITES ON DUPLEX DNA MOLECULES, BY FORMING A COLINEAR TRIPLEX, THE SYNTHETIC OLIGONUCLEOTIDES AND METHODS OF USE

[75] Inventors: Michael E. Hogan; Donald J. Kessler, both of The Woodlands, Tex.

[73] Assignee: Baylor College of Medicine, Houston, Tex.

[21] Appl. No.: 453,532

[22] Filed: Dec. 22, 1989

Related U.S. Application Data

[63] Continuation-in-part of Ser. No. 287,359, Dec. 20, 1988, abandoned.

[51] Int. Cl.$^5$ .................. C12Q 1/68; C12P 19/34; C07H 15/12; G01N 33/00
[52] U.S. Cl. .......................... 435/6; 435/91; 536/24.5; 536/25.1; 436/94
[58] Field of Search ............... 435/6; 536/91, 27, 28; 436/94

[56] References Cited

U.S. PATENT DOCUMENTS

| | | | |
|---|---|---|---|
| 4,469,863 | 9/1984 | Ts'o et al. | 536/27 |
| 4,511,713 | 4/1985 | Miller et al. | 536/27 |
| 4,587,044 | 5/1986 | Miller et al. | 530/211 |
| 4,667,025 | 5/1987 | Miyoshi et al. | 536/27 |
| 4,740,463 | 4/1988 | Weinberg et al. | 435/172 |
| 4,757,055 | 7/1988 | Miller et al. | 514/44 |
| 4,806,463 | 2/1989 | Goodchild et al. | 435/5 |

OTHER PUBLICATIONS

Maniatis et al Molecular Cloning (1982). Cold Spring Harbor Press, CSH NY pp. 229-242.
Firtel et al. Proc Natl Acad Sci 76:6206-6210 (1979).
Asseline, U., et al: Nucleic acid-binding moles with high affinity and base sequence specificity: Intercalating agents covalently linked to oligodeoxynucleotides; Proc. Natl. Acad. Sci. USA, 81:3297-3301 (1984).
Bloomfield, V. A., et al; Physical chemistry of nucleic acids; Harper & Row, Publishers, Inc., New York, 322-333 (1974).
Boidot-Forget, M., et al; Site-specific cleavage of single-stranded and double-stranded DNA sequences by oligodeoxyribonucleotides covalently linked to an intercalating agent and an EDTA-Fe chelate; Gene, 72:361-371 (1988).
Boles, T. C., et al; DNA Structure Equilibria in the Human c-myc Gene; Biochemistry, 26, 367-376 (1987).
Broitman, S. L., et al; Formation of the triple-stranded polynucleotide helix, poly(A.A.U); Proc. Natl. Acad. Sci. USA, 84:5120-5124 (1987).
Chase, M.; Promise Seen in "Anti-Sense" Medicine; The Wall Street Journal, (Aug. 2, 1988).
Chu, B. C. F., et al; Derivatization of unprotected polynucleotides; Nucleic Acids Research, 11:6513-6529 (1983).
Cooney, M. et al: Site-Specific Oligonucleotide Binding Represses Transcription of the Human c-myc Gene in Vitro; Science, 241:456-459 (1988).

(List continued on next page.)

Primary Examiner—Margaret Moskowitz
Assistant Examiner—Scott A. Chambers
Attorney, Agent, or Firm—Fulbright & Jaworski

[57] ABSTRACT

A method for making synthetic oligonucleotides which bind to target sequences in a duplex DNA forming colinear triplexes by binding to the major groove. The method includes scanning genomic duplex DNA and identifying nucleotide target sequences of greater than about 20 nucleotides having either about at least 65% purine bases or about at least 65% pyrimidine bases; and synthesizing synthetic oligonucleotides complementary to identified target sequences. The synthetic oligonucleotides have a G when the complementary location in the DNA duplex has a GC base pair and have a T when the complementary location in the DNA duplex has an AT base pair. The synthetic oligonucleotides are oriented 5' to 4' and bind parallel or 3' to 5' and bind antiparallel to the about at least 65% purine strand.

3 Claims, 7 Drawing Sheets

OTHER PUBLICATIONS

Drinkwater, R. D., et al; Two human repetitive DNA elements: a new interspersed repeat found in the factor IX gene, and a satellite II tandem repeat sequence; Nucleic Acids Research, 14:9541 (1986).

Francois, J., et al; Sequence-specific recognition of the major groove of DNA by oligodeoxynucleotides via triple helix formation. Footprinting studies; Nucleic Acids Research, 16:11431–11440 (1988).

Harel-Bellan, A, et al; Specific inhibition of c-myc protein biosynthesis using an antisense synthetic deoxy-oligonucleotide in human T lymphocytes; The Journal of Immunology, 140–2431-2435 (1988).

Harvey, S. C., et al; DNA stem-loop structures in oligopurine-oligopyrimidine triplexes; Nucleic Acids Research, 16:11795–11809 (1988).

Kohwi, Yoshinori, et al; Magnesium ion-dependent triple-helix structure formed by homopurine-homopyrimidine sequences in supercoiled plasmid DNA; Proc. Natl. Acad. Sci. USA, 85:3781–3785 (1988).

Leder, A., et al; Consequences of Widespread Deregulation of the c-myc Gene in Transgenic Mice: Multiple Neoplasms and Normal Development; Cell, 45:485–495 (1986).

Lyamichev, V. I., et al; Structures of Homopurine-homopyrimidine Tract in Superhelical DNA; Journal of Biomolecular Structure and Dynamics, 3:667–669 (1986).

Matsukura, M., et al; Phosphorothioate analogs of oligodeoxynucleotides; Inhibitors of replication and cytopathic effects of human immunodeficiency virus; Proc. Natl. Acad. Sci. USA, 84:7706–7710 (1987).

Minton, K. W., et al. The Triple Helix: A Potential Mechanism for Gene Regulation; Journal of Experimental Pathology, 2:135–148 (1985).

Moffat, A. S.; Researchers Pursue "Anti-Sense" Technology in Quest for Novel Drugs and Agriproducts; Genetic Engineering News, (1988).

Moser, H. E., et al; Sequence-specific Cleavage of Double Helical DNA by Triple Helix Formation; Science, 238:645–650 (1987).

Praseuth, D., et al; Sequence-specific binding and photocrosslinking of $\alpha$ and $\beta$ oligodeoxynucleotides to the major groove of DNA via triple-helix formation: Proc. Natl. Acad. Sci. USA, 85:1349–1353 (1988).

Rajagopal, P., et al; Triple-strand formation in the homopurine:homopyrimidine DNA oligonucleotides $d(G-A)_4$ and $d(T-C)_4$; Nature, 339:637–640 (1989).

Stein, C. A., et al; Physicochemical properties of phosphorothioate oligodeoxynucleotides; Nucleic Acids Research, 16(8):3209–3221 (1988).

Strobel, S. A., et al; Double-Strand Cleavage of Genomic DNA at a Single Site by Triple-Helix Formation; J. Am. Chem. Soc., 110:7927–7929 (1988).

Vlassov, V. V., et al; Sequence-specific chemical modification of double-stranded DNA with alkylating oligodeoxyribonucleotide derivatives; Gene, 72:13–322 (1988).

Walder, R. Y., et al; Role of RNase H in hybrid-arrested translation by antisense oligonucleotides; Proc. Natl. Acad. Sci. USA, 85:5011–5015 (1988).

Wickstrom, E. L., et al; Human promyelocytic leukemia HL-60 cell proliferation and c-myc protein expression are inhibited by an antisense pentadecadeoxynucleotide targeted against c-myc mRNA; Biochemistry, 1028–1032 (1987).

Zon, G.; Oligonucleotide Analogues as Potential Chemotherapeutic Agents; Pharmaceutical Research, 5:539–549 (1988).

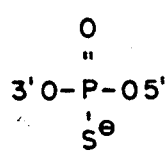  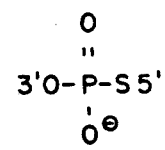 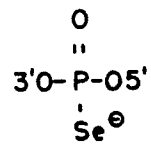
FIG. 4A   FIG. 4B   FIG. 4C   FIG. 4D
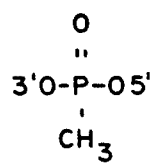 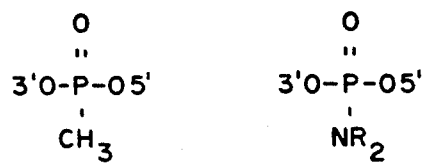 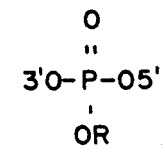 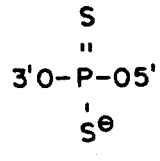
FIG. 4E   FIG. 4F   FIG. 4G   FIG. 4H
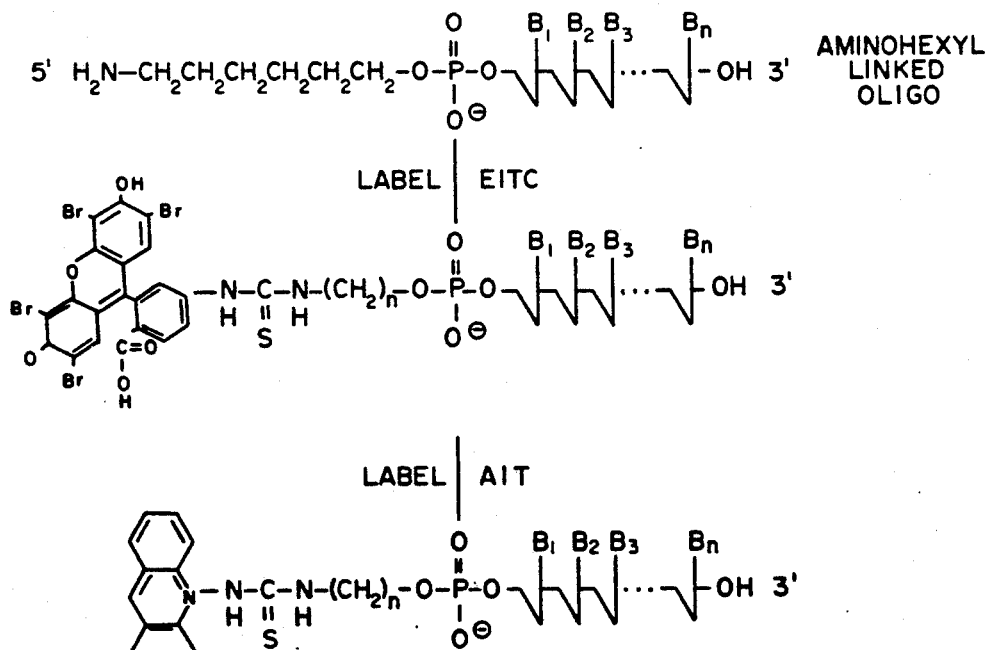
FIG. 5

METHOD FOR MAKING SYNTHETIC OLIGONUCLEOTIDES WHICH BIND SPECIFICALLY TO TARGET SITES ON DUPLEX DNA MOLECULES, BY FORMING A COLINEAR TRIPLEX, THE SYNTHETIC OLIGONUCLEOTIDES AND METHODS OF USE

This application is a Continuation-in-Part of Applicants Co-pending U.S. application Ser. No. 287,359 filed Dec. 20, 1988, now abandoned.

This invention was supported in part through a grant or award from the National Institute of Health.

FIELD OF INVENTION

The present invention relates generally to a method for making synthetic oligonucleotides which bind to the major groove of a duplex DNA to form a colinear triplex. It also relates to synthetic oligonucleotides which bind to the purine strand of a DNA duplex. It further relates to a method of regulating and inhibiting cellular growth by administering a synthetic oligonucleotide which is capable of binding to a DNA duplex to form a colinear triplex.

BACKGROUND ON THE INVENTION

It has been known for some time that the polynucleotide polydT will bind to the polydA-polydT duplex to form a colinear triplex (Arnott, S & Selsing E. (1974) J. Molec. Biol. 88, 509). The structure of that triplex has been deduced from X-ray fiber diffraction analysis and has been determined to be a colinear triplex (Arnott, S & Selsing E. (1974) J. Molec. Biol. 88, 509 ). The polydT strand is bound in the parallel orientation to the polydA strand of the underlying duplex. The polydT-polydA-polydT triplex is stabilized by T-A Hoogstein base pairing between A in the duplex and the third strand of polydT. That interaction necessarily places the third strand, called a ligand, within the major groove of the underlying duplex. The binding site in the major groove is also referred to as the target sequence.

Similarly, it has been shown that polydG will bind by triplex formation to the duplex polydG-polydC, presumably by G-G pairing in the major helix groove of the underlying duplex, (Riley M., Mailing B. & Chamberlin M. (1966) J. Molec. Biol. 20, 359). This pattern of association is likely to be similar to the pattern of G-G-C triplet formation seen in tRNA crystals (Cantor C. & Schimmel P., (1980) Biophysical Chemistry vol I, p. 192–195).

Triplexes of the form polydA-polydA-polydT and polydC-polydG-polydC have also been detected (Broitman S., Im D. D. & Fresco J. R. (1987) Proc. Nat. Acad. Sci USA 84, 5120 and Lee J. S., Johnson D. A. & Morgan A. R. (1979) Nucl. Acids Res. 6, 3073). Further the mixed triplex polydCT-polydGA-polydCT has also been observed. (Parseuth D. et al. (1988) Proc. Nat. Acad Sci. USA 85, 1849 and Moser H. E. & Dervan P. B. (1987) Science 238, 645). These complexes, however, have proven to be weak or to occur only at acid PH.

Parallel deoxyribo oligonucleotide isomers which bind in the parallel orientation have been synthesized (Moser H. E. & Dervan P. E. (1987) Science 238, 645–650 and Rajagopol P. & Feigon J. (1989) Nature 339, 637–640). In examples where the binding site was symmetric and could have formed either the parallel or antiparallel triplex (oligodT binding to an oligodA-oligodT duplex target), the resulting triplex formed in the parallel orientation (Moser H. E. & Dervan P. E. (1987) Science 238, 645–650 and Praseuth D. et al (1988) PNAS 85, 1349–1353), as had been deduced from x-ray diffraction analysis of the polydT-polydA-polydT triplex.

Studies employing oligonucleotides comprising the unnatural alpha anomer of the nucleotide subunit, have shown that an antiparallel triplex can form (Praseuth D. et al. (1988) PNAS 85, 1349–1353). However, since the alpha deoxyribonucleotide units of DNA are inherently reversed with respect to the natural beta subunits, an antiparallel triplex formed by alpha oligonucleotides necessarily follows from the observation of parallel triplex formation by the natural beta oligonucleotides. For example, alpha deoxyribo oligonucleotides form parallel rather than antiparallel Watson-Crick helices with a complementary strand of the beta DNA isomer.

It has been demonstrated that a DNA oligonucleotide could bind by triplex formation to a duplex DNA target in a gene control region; thereby repressing transcription initiation (Cooney M. et. al. (1988) Science 241, 456). This was an important observation since the duplex DNA target was not a simple repeating sequence.

The present invention provides a new method for designing synthetic oligonucleotides which will bind tightly and specifically to any duplex DNA target. When the target serves as a regulatory protein the method can be used to design synthetic oligonucleotides which can be used as a class of drug molecules to selectively manipulate the expression of individual genes.

SUMMARY OF THE INVENTION

The object of the present invention is a method for designing synthetic obligonucleotides which bind to duplex DNA.

A further object of the present invention is a method for making synthetic obliogonucleotides which form triplexes with DNA.

An additional object to the present invention is a synthetic oligonucleotide which forms a colinear triplex with a target sequence in a duplex DNA.

Another object to the present invention is a provision of a synthetic oligonucleotide which inhibits the growth of cells.

A further object of the present invention is a provision of a synthetic oligonucleotide which inhibits the growth of a pathogen.

An additional object of the present invention is a method for altering the structural protein content of epidermal tissue for the treatment of aging and blood clotting.

A further object of the present invention is a method of inhibiting gene expression by permanently altering the DNA sequence.

Thus, in accomplishing the foregoing objects, there is provided in accordance with one aspect of the present invention a method for making a synthetic oligonucleotide which binds to a target sequence in duplex DNA forming a colinear triplex by binding to the major groove, said method comprising the steps of: scanning genomic duplex DNA and identifying nucleotide target sequences of greater than about 20 nucleotides having either about at least 65% purine bases or about at least 65% pyrimidine bases; and synthesizing said synthetic oligonucleotide complementary to said identified target sequence, said synthetic oligonucleotide having a G when the complementary location in the DNA duplex has a GC base pair, having a T when the complementary location of the DNA duplex has an AT base pair. In specific embodiments the synthetic oligonucleotide can be selected from the group consisting of an oligonucleotide oriented 5' to 3' and binding parallel to the about at least 65% purine strand, or an oligonucleotide oriented 3' to 5' and binding anti-parallel to the about at least 65% purine strand.

A further aspect of the present invention is the synthetic oligonucleotide for forming a colinear triplex with a target sequence in a duplex DNA when said target sequence is either about at least 65% purine bases or about at least 65% pyrimidine basis, comprising, a nucleotide sequence of at least about 20 nucleotides; said nucleotide sequence including G and T, wherein G is used when the complementary location and duplex DNA has a GC base pair and T is used when the complementary location in the duplex DNA is an AT base pair; and said sequence selected from the group consisting of an oligonucleotide oriented 5' to 3' and binding parallel to the about at least 65% purine strand of the duplex DNA target sequence, and an oligonucleotide oriented 3' to 5' and binding anti-parallel to the about at least 65% purine strand in the duplex DNA target sequence.

In the preferred embodiments the synthetic oligonucleotide can have at least one T replaced by X, I, and halogenated derivatives of X and I. Furthermore, at least one G can be replaced with halogenated derivatives of G.

Additional embodiments include substitutions on the synthetic oligonucleotide. For example, the base can be substituted at the 2' furanose position with a non-charged bulky group and the backbone of the synthetic oligonucleotide can be a phosphodiester anologue which is not readily hydrolyzed by cellular nucleases. In addition, a linker can be affixed at the 3' and/or 5' terminus of the synthetic oligonucleotide. This linker provides a method for attaching modifying groups to the oligonucleotide. The modifying groups can be intercalators, groove-binding molecules, cationic amines and cationic polypeptides.

Another aspect of the present invention is a method of inhibiting the growth of cells comprising the step of administering synthetic oligonucleotides in sufficient quantity for cellular uptake and binding to the target sequence, wherein said target sequence is positioned within the DNA domain adjacent to the RNA transcription origin. This procedure can be used to inhibit the growth of cancer cells and pathogens. In one preferred embodiment this procedure is used to inhibit HIV-I virus by binding a synthetic oligonucleotide to the viral LTR region.

Another aspect of the present invention is a method of altering the relative proportions of the structural protein content of epidermal tissue by administering a synthetic oligonucleotide in sufficient quantity for cellular uptake and binding to target sequences for collagen genes.

Other and further objects, features and advantages will be apparent from the following description of the presently preferred embodiments of the invention given for the purpose of disclosure when taken in conjunction with the accompanying drawings.

2C and 2D are corresponding bonding patterns which result when the G of a GC base pair or A of an AT pair occurs across from the orienting strand of the target duplex. In that instance, the rules of oligonucleotide sequence selectivity are the same (i.e., G at a GC pair, T at an AT pair) however, G bonding occurs N3 to N9 and T bonds in the "reverse Hoogsteen" way, thereby both retain the overall parallel orientation of the bound ligand and the orienting strand of the target.

FIGS. 3A-3D show one method of improving the pattern of oligonucleotide hydrogen bonding with the duplex target: xanthine binding to AT sites. The computer generated simulation in FIGS. 3A-3D is as in FIGS. 2A-2D, except that the effect of substituting xanthine (X) for T is presented. As seen, in both the "Hoogsteen" binding (3A and 3B) and "Reverse Hoogsteen" (3C and 3D) mode of binding, X and T bind equivalently to an underlying AT base pair. The major difference between the two is that X is nearly identical to the G residues which might flank it in an oligonucleotide ligand, with respect to base size and shape and with respect to the orientation of its phosphodiester component within the oligonucleotide binding site. Modeling predicts that such enhancement of oligonucleotide continuity will enhance the binding affinity and site specificity of all oligonucleotides in which T is replaced by X.

FIGS. 4A-4D display the family of altered phosphodiester linkages compatible with colinear triplex formation. Some of the homologues of the phosphate within the backbone of an oligonucleotide are presented. In each instance, examples are cited which can be prepared by a simple modification of the standard computer assisted, solid phase methods. For example, FIGS. 4A–C and H are thiophosphate linkage, FIG. 4D is phosphoroselenoate, FIG. 4E is methylphosphonate, FIG. 4F is phosphoramidite and FIG. 4G is phosphotriester.

FIG. 5 shows formation of hybrid olionucleotides by means of coupling through a 5' amine linkage. In this instance, a hexylamine linkage is described. This linkage can be affixed as the last residue of an oligonucleotide by employing the same phosphoramidite chemistry used to polymerize the DNA bases. After purificatin of the linker-modified oligonucleotide, groups which selectively react with a primary alkyl amine can be added. These groups include the isothiocyanate derivative of eosin (EITC) or 9 amino acridine (AIT), or any number of other small molocules. Essentially identical chemistry is available for affixing a thiol group to the 5' terminus.

Figures 1A, 1B:
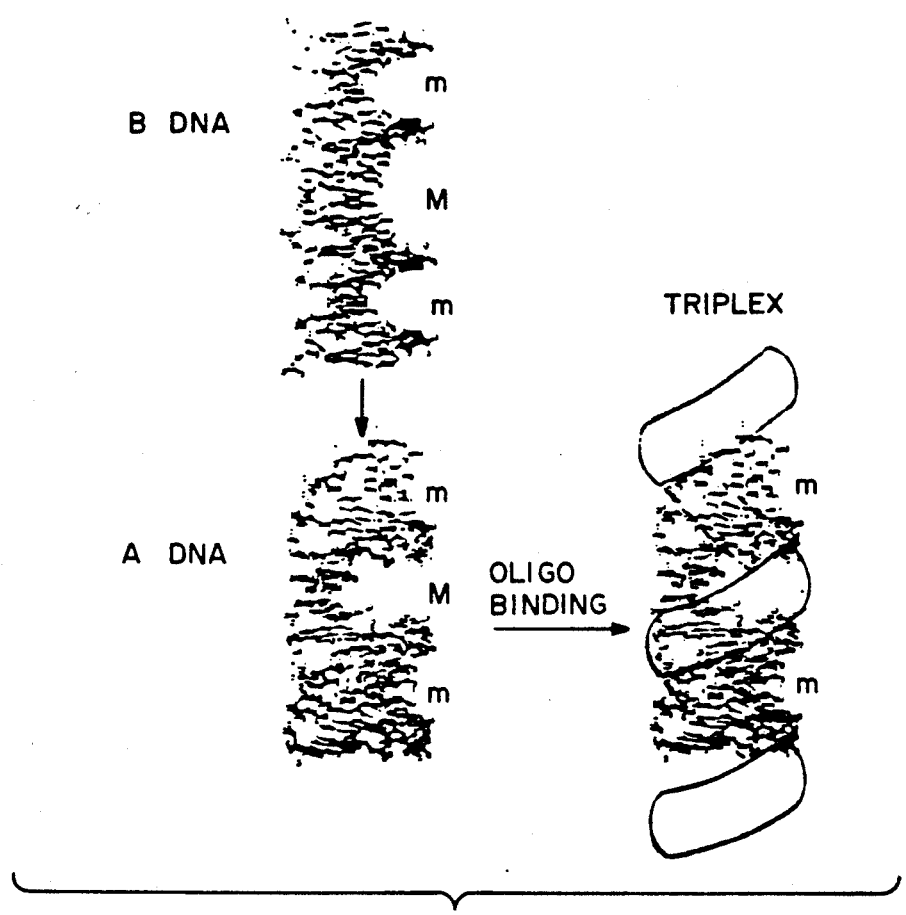
FIG. 1A shows the surface morphology of a colinear triplex. It is a computer generated rendering of the structure of a duplex DNA target site and presents in both the canonical B and A helix form. Upon binding of an oligonucleotide ligand, the target undergoes a transition from the B to the A form, which creates an increase in the depth of the major helix groove (M). In a colinear triplex, the oligonucleotide wraps about the A form helix target, occupying the major groove. The groove binding has been emphasized by presenting the bound oligonucleotide as a ribbon-like abstraction.
FIG. 1B shows the strand orientation in a colinear triplex. The oligonucleotide ligand binds to the duplex target, in the parallel orientation relative to the orienting (more purine rich) strand.
Figure 2A:
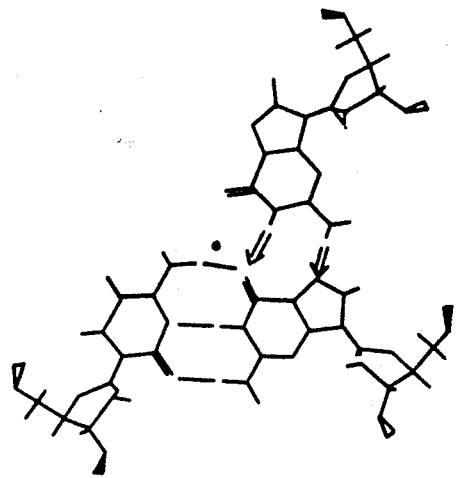
FIGS. 2A-2D show the pattern of oligonucleotide hydrogen bonding with the duplex target: G to GC sites, T to AT sites. 2A is a computer simulated rendering of the preferred pattern of hydrogen bonding between G in the ligand and G in the GC base pair at the corresponding site within the orienting strand of the duplex target. 2B is an equivalent simulation of T binding to the A of an AT base pair at its corresponding site within the orienting strand of the duplex target. The T-AT association is identical to classical "Hoogsteen base pairing", whereas the G-GC association is essentially the quanine counterpart thereof and involves N3 to O6 bonding. Solid wedges define the site at which such a crossection through a triplex is affixed to the corresponding crossection above it. Open wedges define the site at which such a crosssection through a triplex is affixed to the corresponding crossection below. As seen, the connectivity defined by the two bonding schemes is nearly identical. It is also important to recognize that the favored pattern of bond formation between G and GC or T and AT (arrows) cannot be mimicked by any other pattern of base-base association at neutral pH (C can mimic G in acid conditions).
Figure 2B:
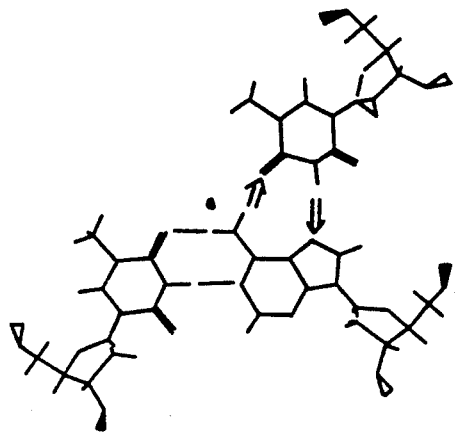
Figure 2C:
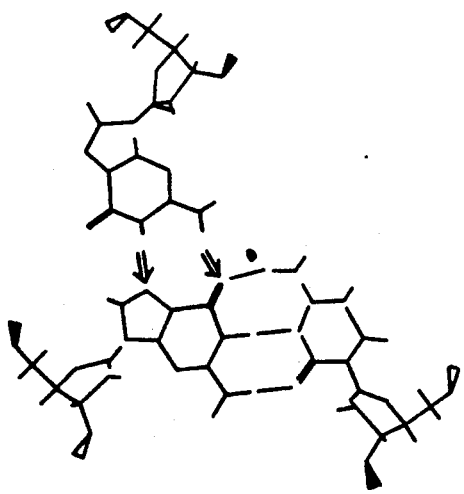
Figure 2D:
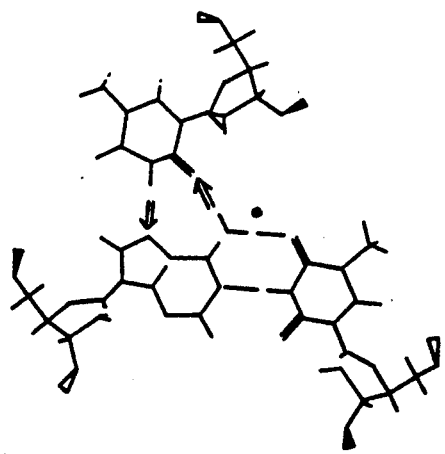
Figure 3A:
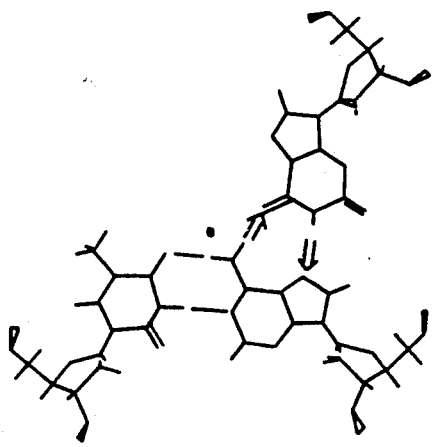
Figure 3B:
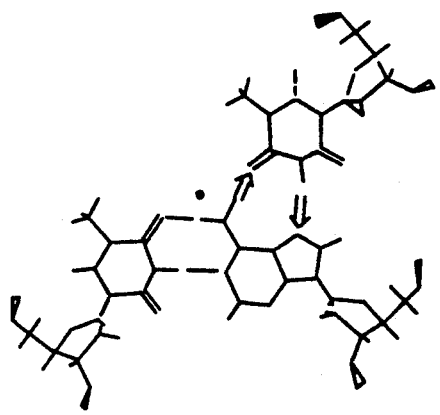
Figure 3C:
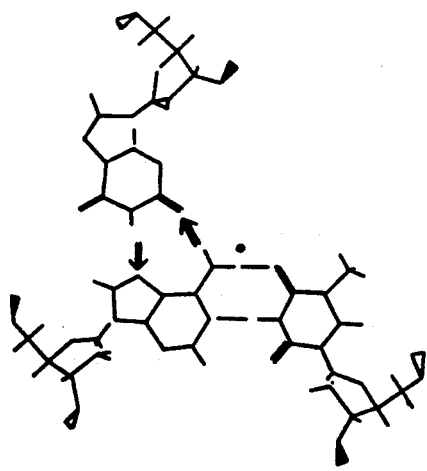
Figure 3D:
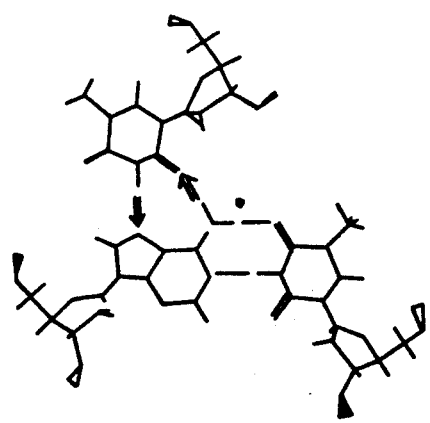
Figure 6:
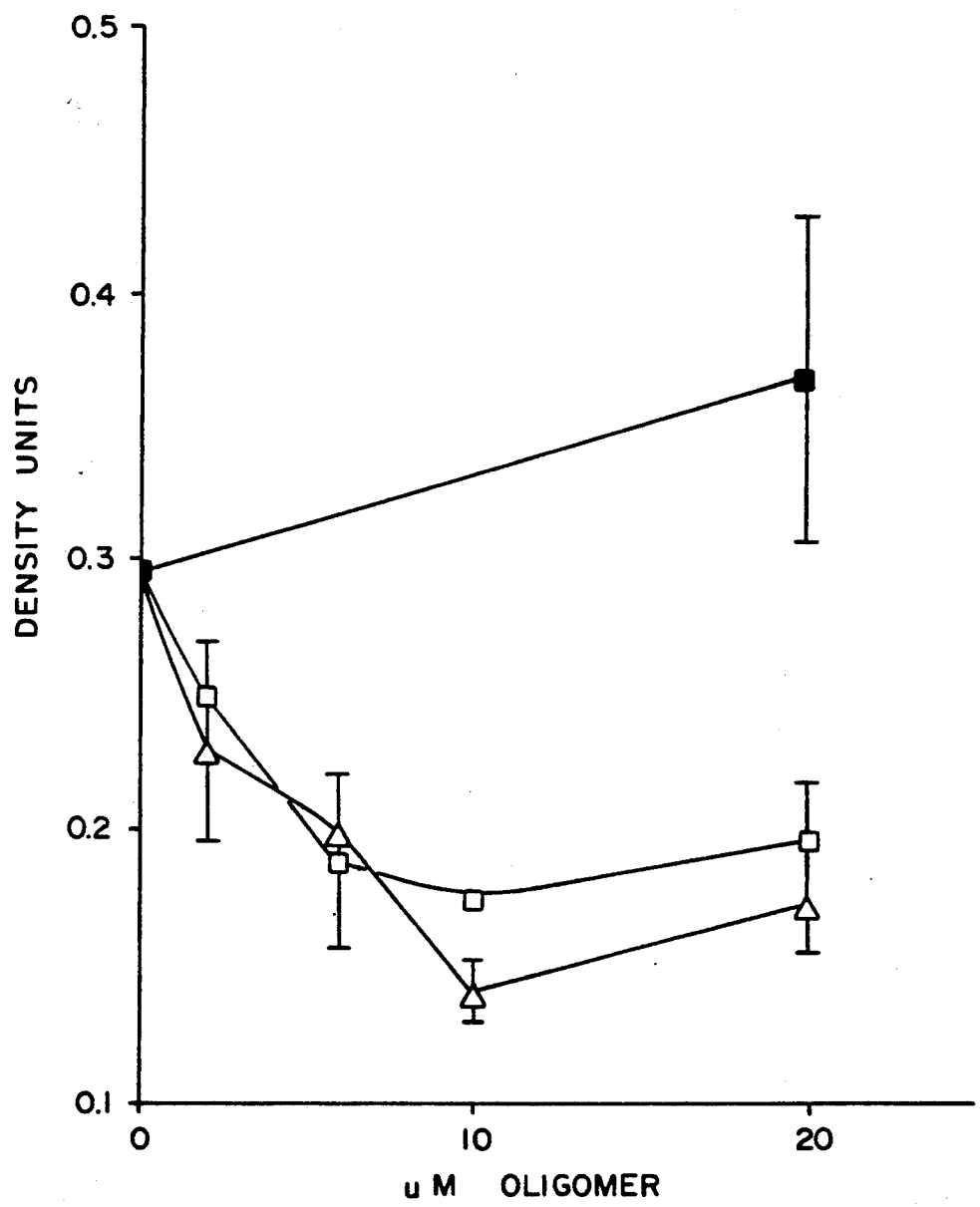

FIG. 6 shows dose dependent inhibition of HIV-1 mRNA by Oligonucleotide mediated DNA triplexes. U937/HIV-1 cells (ATCC CRL 1593, American Type Culture Collection, Rockville, Md.), infected with the HTLV-IIIB prototype strain of HIV-1 and cultured under conditions where >90% of the cells remained viable and contained HIV-1 mRNA as shown by in situ hybridization with the $^{35}$S-labeled probe for the LTR of HIV-1, (NEP 200, DuPont, Wilmington, Del.)] were incubated with each oligonucleotide at 0, 2, 6, 10, and 20 uM concentrations. Oligonucleotide was added to the culture supernatants at the initiation of incubation and again after 2 hours. Cells were harvested after 4 hours incubation, and washed with PBS before harvest of total cellular RNA using RNAzol (Cinna/Biotecx Laboratories International, Inc., Friendswood, Tex.). Serial 2-fold dilutions were made from each RNA preparation (starting at 2.5 ug RNA) and equal amounts were applied to duplicate nylon membranes using a slot blot apparatus (Biorad). One blot was probed with the radiolabeled EcoR1-HhaI env fragment from the HIV-1 containing plasmid pARV-7/2, while the other was probed with radiolabeled cDNA for $\beta$-actin. The resulting autoradiographs were then analyzed by densitometry. The density units expressed on the ordinate express the ratio of (env-probe density)/(actin-probe density). $\Delta$ represent HIV29par, $\square$ represent HIV31 anti, and $\square$ represent random HIV29 isomer.

Figure 7:
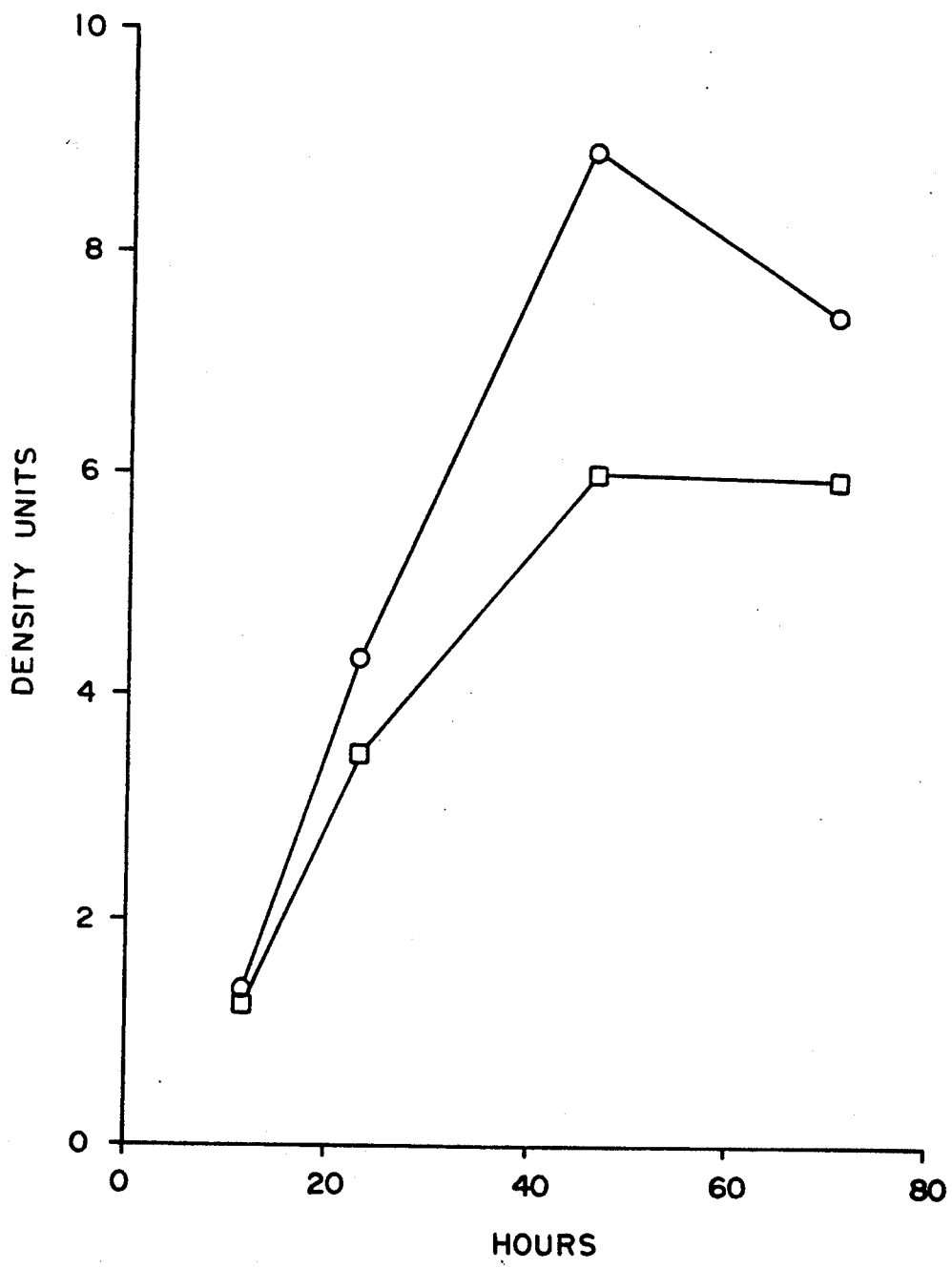

FIG. 7 shows the persistence of the effect of oligonucleotides on HIV infected H9 T cells. HIV-1 infected U937 cells were cultured for 12 to 72 hrs. after the last addition of HIV31anti. The oligonucleotide was added at the initiation of the culture and at 2 hrs. thereafter to maintain a final concentration of 10 $\mu$M. Cells were harvested at the indicated time points thereafter. Total cellular RNA was harvested and applied to duplicate nylon membranes in serial dilution with a slot blot apparatus. One replicate was probed with the HIV-1 env cDNA and the other with the cDNA for $\beta$-actin. The density units (ordinate) are expressed as the ratio of env to $\beta$-actin densitometry readings. $\square$ represent HIV31 anti and O represent controls.

Figure 8:
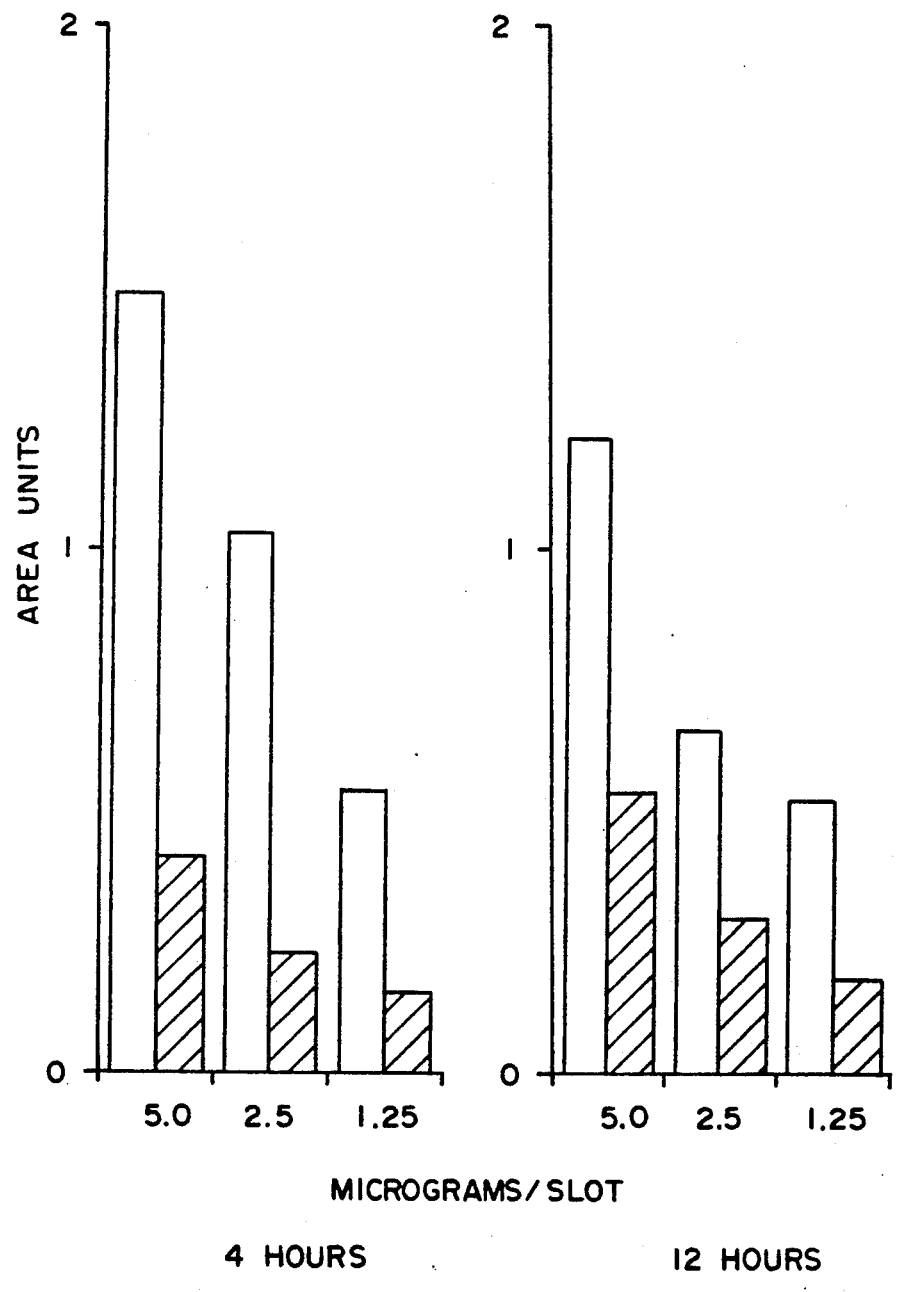

FIG. 8 shows inhibition of viral mRNA by HIV29par in infected H9 cells. The densitometric analysis shows a decrease in specific viral message. H9 cells, infected with HTLV IIIB, were treated with oligomer (5 $\mu$M) every two hours. At four and twelve hours the cells were harvested, washed with PBS, and the total cellular RNA was extracted. The hatched bars represent oligomer treatment and unhatched bars represent controls.

The drawings are not necessarily to scale. Certain features of the invention may be exaggerated in scale or shown in schematic form in the interest of clarity and conciseness.

DETAILED DESCRIPTION

It is readily apparent to one skilled in the art that various substitutions and modifications may be made to the invention disclosed herein without departing from the scope and spirit of the invention.

The term "synthetic oligonucleotides as used herein is defined as a molecule comprised of two or more deoxyribonucleotides or ribonucleotides, preferably more than ten. Its exact size will depend on many factors, including its specificity and binding affinity.

When referring to bases herein the term includes both deoxyribonucleic acids and ribonucleic acids. The following abbreviations are used: "A" refers to adenine as well as its deoxyribose derivatives, "T" refers to thymine as refers to the ribose derivative uracil, "G" refers to quanine as well as its deoxyribose derivative, "C" refers to cytosine as well as its deoxyribose derivative, "X" refers to xanthine as well as its deoxyribose derivative and "I" refers to inosine.

The "major groove" refers to one of the grooves along the outer surface of the DNA helix which is formed because the sugar-phosphate backbone extends further from the axis than the bases do. The major groove is important for binding of regulator molecules to specific DNA sequences.

A set of procedures have been established to design DNA or RNA oligonucleotides which bind specifically to a DNA target by colinear triplex formation. One embodiment of the present invention is a method for making a synthetic oligonucleotide which binds to a target sequence in duplex DNA forming a colinear triplex by binding to the major groove, said method comprising the steps of: scanning genomic duplex DNA and identifying nucleotide target sequences of greater than 20 nucleotides, said target sequences having either about at least 65% purine bases or about at least 65% pyrimidine bases; and synthesizing said synthetic oligonucleotide complementary to said identified target sequence, said synthetic oligonucleotide having a G when the complementary location in the DNA duplex has a GC base pair, having a T when the complementary location in the DNA duplex has an AT base pair. In specific embodiments the synthetic oligonucleotide is selected from the group consisting of an oligonucleotide oriented 3' to 5' and binding anti-parallel to the about at least 65% purine strand and an oligonucleotide oriented 5' to 3' and binding parallel to the about at least 65% purine strand. The resulting oligonucleotide can be synthesized in gram quantities by the standard methods of solid phase oligonucleotide synthesis.

The site-specific oligonucleotide procedure is divided into three parts:
 I. Oligonucleotide base sequence design.
 II. Analysis of the duplex target
 III. Secondary chemical modification of the oligonucleotide.

I. Oligonucleotide base sequence design

After identifying a DNA target with an interesting biological function, an oligonucleotide length must be chosen. There is a one to one correspondence between oligonucleotide length and target length. For example, a 27 base long oligonucleotide is required to bind to a 27 base pair long duplex DNA target. Under optimal conditions, the stability of the oligonucleotide-duplex DNA interaction generally increases continuously with oligonucleotide length. In the preferred embodiment, a DNA oligonucleotide in the range of about 20 to 40 bases is used. Oligonucleotides in this range usually have useful dissociation constants for their specific DNA target. The dissociation constants are in the range of about $10^{-9}$ to $10^{-8}$ molar Oligonucleotides shorter than 20 bases display weaker and less specific binding to the target sequence and are thus less useful.

Oligonucleotide binding to duplex DNA is stabilized by binding to the purines in the underlying duplex. Once a DNA target has been identified, the more purine rich strand of the target area is defined as the "orienting" strand of the binding site. An oligonucleotide ligand was designed to bind either parallel or anti-parallel to the orienting strand. The stability of the binding is dependent on the size of the oligonucleotide and the location in the genome. Sometimes the parallel is more stable than the anti-parallel while at other times the reverse is true or they are equally stable. In the preferred embodiment the method of designing a detailed sequence of an oligonucleotide ligand involves placing a T in the oligonucleotide whenever an AT base pair occurs in the duplex target, and placing a G in the oligonucleotide whenever a GC base pair occurs in the duplex target.

Examples of the orientation of bond donors and acceptors based on this oligonucleotide structure is displayed in FIGS. 2 and 3.

Another embodiment of the present invention includes a synthetic oligonucleotide for forming a colinear triplex with a target sequence in a duplex DNA when said target sequence is either about at least 65% purine bases or about at least 65% pyrimidine bases, comprising, a nucleotide sequence of at least about 20 nucleotides; said nucleotide sequence including G and T, wherein G is used when the complementary location in the duplex DNA is a GC base pair and T is used when the complementary location in the duplex DNA is an AT base pair; and said sequence selected from the group consisting of an oligonucelotide oriented 3' to 5' and binding anti-parallel to the about at least 65% purine strand in the duplex DNA target sequence and an oligonucleotide oriented 5' to 3' and binding parallel to the about at least 65% purine strand in the duplex DNA target sequence. Although molecules which include one or more bases which do not comply with this relationship can be fabricated, the binding affinity and site specificity of these altered oligonucleotides will be reduced. Consequently the biological potency of these molecules will be inferior to the oligonucleotides having the G/GC and T/AT relationships.

Below is a schematic which demonstrates a target sequence, and oligonucleotides ligands which have been designed by the above design procedure.

Target Sequence (35 bp)

5'-GGGAATTGGGCGGGTAATTTCGGGATAGGCGGTAA-3'
3'-CCCTTAACCCGCCCATTAAAGCCCTATCCGCCATT-5'

Parallel Synthetic Oligonucleotide

5'-GGGTTTTGGGGGGGTTTTTTGGGGTTTGGGGGTTT-3' (par)

Anti-Parallel Synthetic Oligonucleotide

3'-GGGTTTTGGGGGGGTTTTTTGGGGTTTGGGGGTTT-5' (anti)

If the synthetic oligonucleotide is constructed with a standard phosphodiester linkage, its binding affinity for the target would be near $10^{-7}$M under physiological conditions of salt, divalent ion concentration and temperature. Since the dissociation constant for oligonucleotide binding to a random DNA sequence population is near $10^{-3}$M for a 35 base oligonucleotide, the synthetic oligonucleotide affinity for the target would be approximately $10^4$ times greater than for random sequence DNA under the same conditions.

II. Analysis of the duplex target

If these procedures are followed to make a synthetic oligonucleotide, any duplex DNA sequence of about at least 65% purines can form a stable triplex. Within a DNA region, although the A+T content is not a significant consideration, duplex DNA sequences which have only purines on the template strand form complexes which in general, are characterized by enhanced stability. If we define n as the number of bases within the template strand which are purine and define (1−n) as the number of pyrimidine bases in the template, then the approximate dissociation constant can be predicted from the following semi-empirical formula:

$$K = \exp^{-[0.4n + (0.2(1-n)/RT)]}$$

This formula assumes near-physiological conditions in vitro, that is 0.05M TRIS/HCL, 5 mM MgCl$_2$, 3 mM spermine PH 7.8, 37° C. These conditions constitute the operating standard used in the design process.

This relationship predicts that an oligonucleotide designed to bind a 35 base long target sequence containing only purine bases in its template strand will form a triplex in which the oligonucleotide binds with a standard dissociation constant of about $1 \times 10^{-10}$M. This dissociation constant will be altered, however, when pyrimidine is in the template strand. In the above schematic representation where the template contains pyrimidine, the dissociation constant is $3 \times 10^{-7}$M.

This relationship is consistent with the observation that the free energy of triplex formation appears to increase in proportion to the span of the target-oligonucleotide interaction and the observation that the binding energy of a G to a GC base pair or a T to an AT base pair is dependant on base pair orientation relative to the template strand.

The molecular origin of that effect can be seen in FIG. 2. It is evident that when the orienting strand comprises a series of purines, the bases in the complementary third strand form a contiguous stacked array. On the other hand, placing a pyrimidine in the orienting strand inverts the base pair. Thus, although third strand hydrogen bonding can still occur with parallel strand orientation upon forming a "Reverse Hoogsteen" bond at the site of inversion, it is associated with a dislocation of the path traversed by the third strand in the major groove. Thus for either an AT or GC base pair, approximately 0.4 kcal of favorable binding free energy results from third strand association at a purine site in the template, but only approximately 0.2 kcal when the third strand binds to a site at which a purine to pyrimidine inversion has occurred.

III. Secondary chemical modification of the oligonucleotide

A. One skilled in the art will recognize that a variety of synthetic procedures are available. In the preferred embodiment the oligonucleotides are synthesized by the phosphoramidite method, thereby yielding standard deoxyribonucleic acid oligomers.

Molecular modeling suggests that substitution of the non-hydrolyzable phosphodiester backbone in the oligonucleotide or elected sites may enhance the stability of the resulting triplex in certain instances. The phosphodiester analogues are more resistant to attack by cellular nucleases. Examples of non-hydrolyzable phosphodiester backbones are phosphorothioate, phosphoroselenoate, methyl phosphate, phosphotriester and the alpha enantiomer of naturally occurring phosphodiester. The thiophosphate and methyl phosphonate linkages are shown in FIG. 4. These non-hydrolyzable derivatives of the proposed oligonucleotide sequences can be produced, with little alteration of DNA target specificity.

Backbone modification provides a practical tool to "fine tune" the stability of oligonucleotide ligands inside a living cell. For example, oligonucleotides containing the natural phosphodiester linkage are degraded over the course of 1-2 hours in eukaryotic cells, while the non-hydrolyzable derivatives appear to be stable indefinitely.

B. Oligonucleotide hybrids provide another method to alter the characteristics of the synthetic oliogonucleotides. Linkers can be attached to the 5' and/or 3' termini of the synthetic oligonucleotide. The linkers which are attached to the 5' terminus are usually selected from the group consisting of a base analogue with a primary amine affixed to the base plane through an alkyl linkage, a base analogue with a sulfhydryl affixed to the base plane through an alkyl linkage, a long chain amine coupled directly to the 5' hydroxyl group of the oligonucleotide and a long chain thiol coupled directly to the 5' hydroxyl group of the oligonucleotide. The linker on the 3' terminus is usually a base analogue with a primary amine affixed to the base plane through an alkyl linkage or a base analogue with a sulfhydryl affixed to the base plane through a alkyl linkage. Affixation of a primary amine linkage to the terminus does not alter oligonucleotide binding to the duplex DNA target.

Once a linkage has been attached to the synthetic oligonucleotide a variety of modifying groups can be attached to the synthetic oligonucleotide. The molecules which can attach include intercalators, groove-binding molecules, cationic amines or cationic polypeptides. The modifying group can be selected for its ability to damage DNA. For example, the modifying group could include catalytic oxidants such as the iron-EDTA chelate, nitrogen mustards, alkylators, photochemical crosslinkers such as psoralin, photochemical sensitizers of singlet oxygen such as eosin, methylene blue, acridine orange and 9 amino acridine and reagents of direct photochemical damage such as ethidium and various pyrene derivatives.

For example an "aminolink", as supplied by Milligen (see FIG. 5) works nicely. However, terminal coupling of any sort is likely to be equivalent. Once synthesized with an aminolink, the modified oligonucleotides can be coupled to any reagent which is specific for a primary amine, for example a succimidate or isothiocyanate moiety (FIG. 5).

In one embodiment, an "aminolink" coupling is used to affix the intercalating dyestuff 9 acridine isothiocanate to triplex forming oligonucleotides. The duplex binding affinity of the oligonucleotide-dye hybrid is approximately 100-fold greater than the oligonucleotide binding affinity. Other embodiments include affixing eosin isothiocyanate to oligonucleotides. Since eosin isothiocyanate cleaves the DNA helix upon irradiation this hybrid oligonucleotide cuts the helix at its binding site when irradiated. This hybrid-oligonucleotide is useful for identifying the oligonucleotide binding site both in vitro and in vivo and potentially can be used as a therapeutic tool for selective gene target destruction.

Photochemical reactivity is also achieved by affixation of psoralin derivatives to oligonucleotides through a 5' linkage. Psoralin binds covalently to DNA after irradiation, and as a consequence is a potent cytotoxic agent. Thus, photochemical reactivity, with oligonucleotide sensitivity provides a tool to direct the toxic psoralin lesion to the oligonucleotide target site.

Similar oligonucleotide coupling is used to target toxic chemical reactivity to specific DNA sequences. Examples include catalytic oxidants such as transition metal chelates and nucleases.

Photochemical reactivity and/or toxic chemical agents can be used to permanently inhibit gene expression.

In addition to chemical reactivity, modifications of oligonucleotides alter the rate of cellular uptake of the hybrid oligonucleotide molecules. The uptake process is rapid, but poorly understood. Terminal modification provides a useful procedure to modify cell type specificity, pharmacokinetics, nuclear permeability, and absolute cell uptake rate for oligonucleotide ligands.

C. Modified base analogues provide another means of altering the characteristics of the synthetic oligonucleotide. Although a purine rather than a pyrimidine, X is identical to T with respect to its capacity to form hydrogen bonds. Molecular modeling has shown that substitution of X for T in the above oligonucleotide design procedures, results in a modified triplex that is much more stable. The increased stability is due principally to enhanced stacking and to an enhancement of phosphodiester backbone symmetry within the ligand. Examples of base substitutions for T are X, I and halogenated X and I. G can be replaced by halogenated G. Furthermore, the 2' furanose position on the base can have a non-charged bulky group substitution. Examples of non-charged bulky groups include branched alkyls, sugars and branched sugars. In the preferred embodiment at least one base is substituted.

Molecular modeling suggests that oligonucleotide design will produce ligands with target affinity and specificity which exceeds that of even the most specific antigen-monoclonal antibody interaction.

Synthetic oligonucleotides have been designed to the transcription control region of the human c-myc protooncogene, to the regulation sequence of collagen Iα, to bind to the TATA box segment of the chicken alpha actin gene, and to bind to an enhancer sequence within the early gene region of human HIV-I.

A further embodiment of the present invention is a method of inhibiting the growth of cells, comprising the step of administering a synthetic oligonucleotide in sufficient amount for cellular uptake and binding to the target sequence, wherein said target sequence is positioned within the DNA domain adjacent to the RNA transcription origin. The synthetic oligonucleotide is as described above in the description of the design process. Uptake into the cells is rapid for these synthetic oligonucleotides and can be altered with the appropriate substitutions and modifications. Similarly the binding can be altered by appropriate changes to the synthetic oligonucleotide. The inhibition of cell growth can be used in the treatment of cancerous cells. Additions of the specific oligonucleotide will selectively inhibit cell growth. For example synthetic oligonucleotides to the c-myc gene can be used to inhibit some cancerous cell growth. Examples of synthetic oligonucleotide which inhibit c-myc expression include: 3'-TGGTGTGTGGGTTTTGTGGG GGGTGGGGGGGTTTTTTTTGGGTGGG-5 and/or 3'-TGTGGTGGGGTGGTTGGGGTGGGTGGGGT-GGGTGGG-5' and/or 5'-TTTGGTGTGGGGGTGGGGGTTTTGTTTTTT-GT-3' and/or 3'-GGTTGGGGTGGGTGGGGTGGGTGGGGT-5' and/or 5'-GGTTGGGGTGGGTGGGGTGGGTGGGGT-3' and fragments and analogues thereof.

Another embodiment includes a method of inhibiting the growth of pathogens comprising the step of administering a synthetic oligonucleotide in sufficient amount for cellular uptake and binding to the target sequence, wherein said sequence binds within the nucleic acid domain adjacent the RNA transcription origin. For example HIV-1 virus can be inhibited with a synthetic oligonucleotide which selectively binds to the viral LTR region. Specific examples of this synthetic oligonucleotide can include 3'-GTTTTTGGGTGTTGTGGGTGTGTGTGGTT-5' and/or 5'-TGGGTGGGGTGGGGTGGGGGGGTGTGGG-GTGTGGGGTG-3' and fragments and analogues thereof.

An additional embodiment includes a method of manipulating the structural protein content of epidermal tissue comprising the step of administering a synthetic oligonucleotide in sufficient amount for cellular uptake and binding to the target sequence. This includes inhibiting the various enzymes and regulating proteins in skin. For example, the collagen Iα gene synthesis rate can be altered by using 3'-TGGGTTGGGTGGTGGTGGGGGTGTGGTTT-GGTTGTGGGTTTTT-5' and/or 3'-GTGGGTTGGGTGGTGGTGGGGGTGTGGTT-TGG-5' and fragments and analogues thereof as the synthetic oligonucleotide. Similarly the collagenase gene can be inhibited by using 5'GGTTGGGGTTGGTGTGTTTTTTTTGTGTG-GGTG-3' and/or 5'-TTGTGGTTGTTTTTTTGGTTGTGTGTGT-3' and fragments and analogues thereof.

The following examples are offered by way of illustration and are not intended to limit the invention in any manner. The synthetic oligonucleotides described in the examples can include any of the substitutions discussed earlier. The backbone, base, linkers and modifying groups can be added. These substitutions will enhance the affinity, the chemical stability, and the cellular uptake properties of the specific oligonucleotide treatments.

EXAMPLE 1

A. A Method For Arresting the Growth of Cancerous Tissue in Man, by Means of Intervention into the Program of c-myc Gene Expression Available evidence suggests that a family of tumors, including Burkitt's lymphoma and others, share a common genetic lesion, which is evident as constitutive overproduction of the c-myc mRNA and its corresponding c-myc protein. Because the c-myc protein has been shown to be a critical element in the control of cell growth, it is believed that there may be a direct causal relation between the overproduction of c-myc protein and uncontrolled cancerous growth for such cells.

In both cancerous and normal cells, the c-myc gene possesses several target sequences within its 5' flanking sequence which satisfy the synthetic oligonucleotide design criteria. In a program of drug development, these target sequences and others are used as templates to direct oligonucleotide design. The purpose of these oligonucleotides is to selectively inhibit c-myc transcription, thereby repressing the uncontrolled growth of tumors with the c-myc lesion.

Three representative target sequences in the transcription control region of the human c-myc gene are shown below:

A. TARGET: THE TATA BOX FOR THE C-MYC GENE

DNA TARGET DUPLEX

```
                                                                  -61                                                    -16
              5'-TCCTCTCTCGCTAATCTCCGCCCACCGGCCCTTTATAATGCGAGGG-3'
              3'-AGGAGAGAGCGATTAGAGGCGGGTGGCCGGGAAATATTACGCTCCC-5'
```

PARALLEL SYNTHETIC OLIGONUCLEOTIDE SEQUENCE

3'-TGGTGTGTGGGTTTTGTGGGGGGTGGGGGGGTTTTTTTTGGGTGGG-5'

ANTI-PARALLEL SYNTHETIC OLIGONUCLEOTIDE SEQUENCE

5'-TGGTGTGTGGGTTTTGTGGGGGGTGGGGGGGTTTTTTTTGGGTGGG-3'

B. TARGET: TRANSCRIPTION ACTIVATOR BINDING SITE—THE PRINCIPAL ACTIVATING PROTEIN BINDING SITE OF THE C-MYC GENE PROMOTER

Inappropriately high levels of c-myc gene expression are strongly associated with the incidence of a variety of human tumors. The triplex oligonucleotides described here were designed to selectively repress the expression of the c-myc gene in such tumors, thereby slowing tumor growth.

(1) DNA TARGET DUPLEX

```
   -153                                          -116
5'-TCT CCT CCCC ACCT T CCCC ACCCT CCCC ACCCT CCCCA-3'
3'-AGA GGA GGGGT GGA AGGGGT GGGA GGGGT GGGA GGGGT-5'
```

ANTI-PARALLEL SYNTHETIC OLIGONUCLEOTIDE

5'-GTGGTGGGGTGGTTGGGGTGGGTGGGGTGGGTGGGGT-3

(2) DNA TARGET DUPLEX

```
   -153                                          -116
5'-TCT CCT CCCC ACCT T CCCC ACCCT CCCC ACCCT CCCCA-3'
3'-AGA GGA GGGGT GGA AGGGGT GGGA GGGGT GGGA GGGGT-5'
```

PARALLEL SYNTHETIC OLIGONUCLEOTIDE SEQUENCE

3'-GTGGTGGGGTGGTTGGGGTGGGTGGGGTGGGTGGGT-5'

(3) DNA TARGET DUPLEX (27 bp)

```
   -142                                -115
5'-CCTT CCCC ACCCT CCCC ACCCT CCCCA-3'
3'-GGAA GGGGT GGGA GGGGT GGGA GGGGT-5'
```

PARALLEL SYNTHETIC OLIGONUCLEOTIDE SEQUENCE

3'-GGTTGGGGTGGGTGGGGTGGGTGGGGT-5' (par)

ANTI-PARALLEL SYNTHETIC OLIGONUCLEOTIDE

5'-GGTTGGGGTGGGTGGGGTGGGTGGGGT-3' (anti)

The 27 bp target duplex has 74% GC base pairs and 89% purine on the orienting strand. The Kdiss is $(6 \times 10^{-10}M)$ for anit-parallel binding.

C. TARGET: SEQUENCE BETWEEN TATA BOX AND ACTIVATOR SITE IN A HIGHLY CONSERVED SEQUENCE AMONG THE VERTEBRATE c-myc GENE FAMILY DNA TARGET DUPLEX
```
   -87                             -58
5'-AAAGCAGAGGGCGTGGGGGAAAAGAAAAAAGA-3'
3'-TTTCGTCTCCCGCACCCCCTTTTCTTTTTTCT-5'
```

PARALLEL SYNTHETIC OLIGONUCLEOTIDE SEQUENCE

5'-TTTGGTGTGGGGGTGGGGGTTTTGTTTTTTGT-3'

ANTIPARALLEL SYNTHETIC OLIGONUCLEOTIDE SEQUENCE

3'-TTTGGTGTGGGGGTGGGGGTTTTGTTTTTTGT-5'

The likely function of these sites, the position relative to the RNA transcription origin, and the oligonucleotide sequence which can be used as a c-myc specific treatment are shown. One skilled in the art will readily recognize that as the molecular genetics of the c-myc gene is elucidated in greater detail, the list of target sequences within the 5' flanking region will be expanded, by application of the above design criteria.

Both synthetic oligonucleotides A and B specifically interact within the target duplex to inhibit tumor growth, by means of specific repression of c-myc transcription. The specific method of inhibition of oligonucleotide C is unknown.

One skilled in the art will readily recognize that oligonucleotides for other genes involved in human tumors can be similarly designed. The procedure is only limited by the available molecular sequence data.

EXAMPLE 2

A Method for Manipulating the Structural Protein Content of Epidermal Tissues, for the Purpose of Altering Tissue Appearance and Wound Healing The structural proteins which define the mechanical properties of skin are well known. The molecular structure of the collagen and elastin proteins and their corresponding proteases, collagenase and elastase, have been intensley studied. These proteins are under the control of an elaborate program of regulation, which appears to change during the wound healing process and as a result of the aging process. The molecular structure is sufficiently defined to consider treatments based upon gene-specific intervention into the pattern of structural protein synthesis and/or enzymatic degradation.

Data suggest that the change in the mechanical properties of skin which accompanies aging (wrinkling, etc.)

is due in part to an age-specific change in the relative abundance of the collagens and other structural proteins. Interference with the synthesis and/or selective degradation of these proteins by drug treatment can reestablish a distribution which approximates that of younger tissue, and thus the effects of aging can be partially reversed.

A program of synthetic oligonucleotide design, based upon manipulation of collagen I synthesis in human skin is described below. By altering the relative protein concentrations the structure and mechanical properties of skin can be altered. Thus the synthetic oligonucleotide can be used as a therapeutic agent to alter the skin aging process or to alter the wound healing process. One skilled in the art will readily recognize that the concepts can be extended to other collagens, to other skin proteins and to their complementary proteases based upon the availability of the necessary genetic data.

Representative target sequences in the transcription control region of the human alpha 1(I) collagen gene, the likely function of those sites, their position relative to the RNA transcription origin, and the synthetic oligonucleotide sequence designed for collagen specific treatment as shown below. As the molecular genetics of the collagen gene develops, the list of target sequences within the 5' flanking region will be expanded.

A. TARGET: THE CAT BOX FOR THE COLLAGEN GENE

DNA TARGET DUPLEX

```
    −168                                               −124
5'-TCCCTTCCCTCCTCCTCCCCCTCTCCATTCCAACTCCCAAATT-3'
3'-AGGGAAGGGAGGAGGAGGGGGAGAGGTAAGGTTGAGGGTTTAA-5'
```

SYNTHETIC OLIGONUCLEOTIDE SEQUENCE

3'-TGGGTTGGGTGGTGGTGGGGGTGTGGTTTGGTTGTGGGTTTTT-5'

B. TARGET: ENHANCER FOR THE COLLAGEN GENE

DNA TARGET DUPLEX

```
   −294                           −264
5'-CCCTACCCACTGGTTAGCCCACGCCATTCT-3'
3'-GGGATGGGTGACCAATCGGGTGCGGTAAGA-5'
```

SYNTHETIC OLIGONUCLEOTIDE SEQUENCE

3'-GGGTTGGGTGTGGTTTGGGGTGGGGTTTGG-5'

C. TARGET: HIGHLY CONSERVED POLYPURINE SEGMENT WHICH OCCURS NEAR −200 IN ALL COLLAGENS

DNA TARGET DUPLEX

```
   −177                        −136
5'-CTCCCTTCCCTCCTCCTCCCCCTCTCCATTCC-3'
3'-GAGGGAAGGGAGGAGGAGGGGGAGAGGTAAGG-5'
```

SYNTHETIC OLIGONUCLEOTIDE SEQUENCE

3'-GTGGGTTGGGTGGTGGTGGGGGTGTGGTTTGG-5'

Synthetic oligonucleotides A and B inhibit type I collagen protein synthesis. The process includes the specific repression of collagen RNA transcription. The method of inhibition of the C synthetic oligonucleotide is not known. The effect on protein synthesis of skin proteins can be seen by adding sufficient amounts of the synthetic oligonucleotide for uptake into cultured human fibroblasts.

Next, two representative target sequences are described in the transcription control region of the human collagenase gene, the function of these sites, their position relative to the RNA transcription origin, and the oligonucleotide sequence designed as a collagen specific treatment. As the molecular genetics of the collagenase gene develops, the list of target sequences within the 5' flanking region will be expanded.

D. TARGET: THE TATA BOX FOR THE COLLAGENASE GENE

DNA TARGET DUPLEX

```
          −48                       −16
5'-GGAAGGGCAAGGACTCTATATATACAGAGGGAG-3'
3'-CCTTCCCGTTCCTGAGATATATATGTCTCCCTC-5'
```

SYNTHETIC OLIGONUCLEOTIDE SEQUENCE

5'-GGTTGGGGTTGGTGTGTTTTTTTTGTGTGGGTG-3'

E. TARGET: THE INDUCIBLE ENHANCER FOR THE COLLAGENASE GENE. CONFIRS TPA TUMOR PROMOTOR RESPONSIVENESS

DNA TARGET DUPLEX

```
       −91                      −64
5'-AAGAGGATGTTATAAAGCATGAGTCAGA-3'
3'-TTCTCCTACAATATTTCGTACTCAGTCT-5'
```

SYNTHETIC OLIGONUCLEOTIDE SEQUENCE

5'-TTGTGGTTGTTTTTTTGGTTGTGTGTGT-3'

The D synthetic oligonucleotide inhibits collagenase protein synthesis. The process includes specific repression of collagenase RNA transcription. The E synthetic oligonucleotide causes loss of TPA sensitivity, and a subsequent repression of collagenase syntheses in the presence of promotors such as TPA. This process includes specific repression of collagenase RNA transcription. Synthetic oligonucleotide interaction will cause collagen protein levels in the cell to rise, as collagenase levels fall. The clinical effect of the increase should cause a useful alteration of the mechanical properties of skin. The effects can be seen by adding sufficient amounts of oligonucleotide for cellular uptake to cultured human fibroblasts.

One skilled in the art will readily appreciate that these concepts can be extended to other genes which are known to be involved in skin development, repair and aging and is only limited by the available molecular genetic data.

EXAMPLE 3

A Method to Repress the Growth of Human HIV-1 Virus, by means of Oligonucleotide Binding to Target Sites within the HIV-1 LTR The HIV-1 virus is known to be the causative agent in human acquired immune deficiency syndrome (AIDS). The long terminal repeat of the HIV-1 virus is known to possess several DNA segments within the LTR region which are required for transcription initiation in a human T-cell host. The synthetic oligonucleotides selectively repress HIV-1 mRNA synthesis in a human host cell, by means of triplex formation upon target sequences within the viral LTR. Repression of an RNA synthesis results in the reduction of the growth rate of the virus. This could result in the slowing of the infection process or the repression of the transition from latency to virulent growth. Most of the sites within the LTR will comprise target sites for drug (oligonucleotide) intervention. There is no wasted DNA in the small, highly conserved LTR region.

Representative target sequences in the transcription control region of the human HIV-1 LTR, the likely function of these sites, their position relative to the RNA transcription origin, and the oligonucleotide sequence designed as a HIV-1 specific treatment are shown below. As the molecular genetics of HIV-1 develops, the list of target sequences within the LTR and elsewhere will be expanded.

In all instances, both the parallel and antiparallel isomers are described. The reason is that, although one or the other will always display the better binding affinity in vitro, the efficacy of each must be tested in vivo to make the final decision.

A. TARGET: THE 5' END OF THE HIV-1 LTR DOMAIN

DNA Target Duplex (25bp, 92% Purine)

```
 -470                       -446
5'-AAAAGAAAAGGGGGGACTGGAAGGG-3'
3'-TTTTCTTTTCCCCCCTGACCTTCCC-5'
```

PARALLEL SYNTHETIC OLIGONUCLEOTIDE SEQUENCE

5'-TTTTGTTTTGGGGGGTGTGGTTGGG-5' (HIV1par)

ANTI-PARALLEL SYNTHETIC OLIGONUCLEOTIDE SEQUENCE

3'-TTTTGTTTTGGGGGGTGTGGTTGGG-5' (HIV1anti)

B. TARGET SITE: A segment of the negative HIV1 regulatory domain, with similarity to a homologous domain in interleukin 2 gene DNA Target Duplex (33bp, 88% purine)

```
5'-AGAGAAGGTAGAAGAGGCCAATGAAGGAGAGAA-3'
3'-TCTCTTCCATCTTCTCCGGTTACTTCCTCTCTT-5'
```

PARALLEL SYNTHETIC OLIGONUCLEOTIDE SEQUENCE

5'-TGTGTTGGTTGTTGTGGGGTTTGTTGGTGTGTT-3' (HIV2par)

ANTI-PARALLEL SYNTHETIC OLIGONUCLEOTIDE SEQUENCE

3'-TGTGTTGGTTGTTGTGGGGTTTGTTGGTGTGTT-5' (HIV2anti)

C: TARGET SITE: A site near the center of the LTR

DNA Target Duplex (25bp, 88% purine)

```
 -229                       -205
9327                        9351
5'-GGGATGGAGGACGCGGAGAAAGAAG-3'
3'-CCCTACCTCCTGCGCCTCTTTCTTC-5'
```

PARALLEL SYNTHETIC OLIGONUCLEOTIDE SEQUENCE

5'-GGGTTGGTGGTGGGGGTGTTTGTTG-3' (HIV3par)

ANTI-PARALLEL SYNTHETIC OLIGONUCLEOTIDE SEQUENCE

3'-GGGTTGGTGGTGGGGGTGTTTGTTG-5' (HIV3anti)

D. TARGET SITE

Binding site for the Sp1-line transcription activator.

(1) DNA Target Duplex (36bp, 78% purine)

```
 -80                                    -51
5'-AGGGAGGCGTGGCCTGGGCGGGACTGGGGAGTGGCG-3'
3'-TCCCTCCGCACCGGACCCGCCCTGACCCCTCACCGC-5'
```

PARALLEL SYNTHETIC OLIGONUCLEOTIDE SEQUENCE

5'-TGGGTGGGGTGGGGTGGGGGGGTGTGGGGTGTGGGG-3' (HIV4par) or (HIV36par)

ANTI-PARALLEL SYNTHETIC OLIGONUCLEOTIDE SEQUENCE

3'-TGGGTGGGGTGGGGTGGGGGGGTGTGCCCTCTGGGGT-5' (HIV4anti) or (HIV36anti)

The HIV4 par also functions if TG is added to the 3' end to make HIV38 par.

E. TARGET: BINDING SITE FOR THE TRANSCRIPTION ACTIVATOR REGION (tar); THE DOWNSTREAM HALF OF THE tar SITE DNA TARGET DUPLEX (29-31bp, 72% purine)

```
      -16                        +13
5'-CTTTTTGCCTGTACTGGGTCTCTCTGGTTAG-3'
3'-GAAAAACGGACATGACCCAGAGAGACCAATC-5'
```

PARALLEL SYNTHETIC OLIGONUCLEOTIDE SEQUENCE

3'-GTTTTTGGGTGTTGTGGGTGTGTGTGGTT-5'  (HIV29par)

ANTI-PARALLEL SYNTHETIC OLIGONUCLEOTIDE SEQUENCE

5'-GTTTTTGGGTGTTGTGGGTGTGTGTGGTTTG-3'  (HIV31anti.)

The oligonucleotides, HIV29par and HIV31anti, were designed as previously described herein. HIV31anti also functions if bases two TG are removed from the 3' end. The relative mobility and DNA footprint analyses of both oligonucleotides show binding with high affinity to target proviral sequences, in vitro.

HIV-1 infected U937 cells, a monocytoid line, were treated with up to 20 μM with either HIV29par, HIV31anti, or a random isomer of HIV29 with no detectable in vitro affinity for the target sequence. Significant inhibition of viral mRNA production, as shown by the decrease in the relative concentrations of env as compared to β-actin mRNA, was achieved at a dose of 10 μM of either oligonucleotide ($p<.01$, paired t-test, FIG. 6). No additional suppression was observed at 20 μM. The random isomer of HIV29 did not inhibit viral mRNA synthesis, even at 20 μM, confirming the specificity of the suppression achieved with HIV29.

We found that when U937/HIV-1 cells were incubated in media containing 0.6 uM $^{32}$P-labeled HIV29-par, the cells were able to rapidly sequester the oligomer in concentrations exceeding that of the media. Assuming an average cell volume of 350 fL, it was determined that the intracellular concentration increased from 2.4 μM after 10 minutes to a plateau of about 6 μM after 2 hours. The oligonucleotides had a prolonged effect on HIV-1 transcription in that two treatments, spaced two hours apart, inhibited viral mRNA synthesis for up to 72 hrs (FIG. 7). Further studies showed the effect of tar sequence specific oligonucleotides on infected T cells. HIV29par was used to treat HIV-infected H9 T cells. Treatment every 2 hrs. with 5 μM effectively suppressed mRNA synthesis in HIV-1 infected H9 T cells at 2 and 12 hours.

Thus, the evidence shows that the oligonucleotides designed to bind within the major groove of the DNA helix, and form triplexes with specific gene sequences in the tar region of the HIV-1 provirus are readily taken up by HIV-1 infected cells and selectively suppress synthesis of HIV-1 mRNA without concomitant suppression of mRNA for β-actin, which constitutive expressed in these cells. With inhibition of viral MNRA synthesis, translation of virus-encoded proteins is also suppressed. Inhibition of viral mRNA depended on the dose of oligonucleotide added; maximum inhibition occurred at concentrations $\geq 10$ μM. The oligonucleotides designed to bind to specific sequences in the DNA duplex and form colinear triplex with the targeted sequences provide an efficient and highly specific agent for regulating gene expression, such agents provide a new class of rationally designed chemotherapeutic agents for controlling virus replication and other processes depend upon new mRNA production.

The synthetic oligonucleotides in A through E will inhibit HIV-I mRNA synthesis, hence viral growth. The process includes specific repression of RNA transcription from the viral LTR.

One skilled in the art will readily recognize that these concepts can be extended to other genes which are known to be involved in the infection process by which HIV-I and other viruses act.

EXAMPLE 4

A Method for Altering Chicken Skeletal Actin Transcription

A representative target sequence in the transcriptions control region of the chicken skeletal alpha actin gene, the function of that site, its position relative to the RNA transcription origin, and the oligonucleotide sequence which would be designed as an actin specific treatment are shown below. As the molecular genetics of the actin gene develops, the list of target sequences within the actin control region will be expanded.

A. TARGET: THE TATA BOX FOR THE CHICKEN SKELETAL ALPHA ACTIN GENE

DNA TARGET DUPLEX

```
      -30                           -4
5'-GATAAAAGGCTCCGGGGCCGGCGGCGG-3'
3'-CTATTTTCCGAGGCCCCGGCCGCCGCC-5'
```

SYNTHETIC OLIGONUCLEOTIDE SEQUENCE

5'-GTTTTTTGGGTGGGGGGGGGGGGGGG-3'

This synthetic oligonucleotide molecule inhibits actin protein sythesis, by specific repression of RNA transcription. This inhibition can be assessed in cultured chicken myoblasts. The intact chicken will show a change in the quality of actin and other muscle proteins whose synthesis if strongly coupled to actin expression. The practical result of this change will be an alteration of the properties of chicken meat.

One skilled in the art will readily appreciate that these concepts can be extended to other genes which are known to be involved in muscle growth and development, and is limited by the available molecular genetic data.

EXAMPLE 5

Interleukin 2 Alpha Chain Receptor

TARGET: TRANS PROMOTOR REGION

DNA Target Duplex (28bp)

-continued

5'-AACGGCAGGGGAATCTCCCTCTCCTTTT-3'  -273 ... -246
3'-TTGCCGTCCCCTTAGAGGGAGAGGAAAA-5'

Parallel Synthetic Oligonucleotide

5'-TTGGGGTGGGGTTTGTGGGTGTGGTTTT-3'  (IL28par)

Anti-Parallel Synthetic Oligonucleotide

3'TTGGGGTGGGGTTTGTGGGTGTGGTTTT-5'  (IL28anti)

The 28 bp target is comprised of 54% G+C base pairs and is 61% purine on the orienting strand. The Kdiss for the parallel stand is $1.5 \times 10^{-7}$ and the Kdiss for the antiparallel is $8 \times 10^{-7}$.

EXAMPLE 6

A Sequence For Dispersing Plaque Formation in Alzeheimers Disease

The APP770 Gene is the precursor protein responsible for production of plaque in Alzheimers disease.

A. TARGET SITE: DOWNSTREAM TATA BOX SITE

DNA Duplex Target

```
       -712                                    -679
5'-AAAAACAAACAAAAATATAAGAAAGAAACAAAA-3'
3'-TTTTTGTTTGTTTTTATATTCTTTCTTTGTTTT-5'
```

PARALLEL SYNTHETIC OLIGONUCLEOTIDE SEQUENCE

5'-TTTTTGTTTGTTTTTTTTTTGTTTGTTTGTTTT-3'  (APPI par)

ANTI-PARALLEL SYNTHETIC OLIGONUCLEOTIDE SEQUENCE

3'-TTTTTGTTTGTTTTTTTTTTGTTTGTTTGTTTT-5'  (APPI anti)

B. TARGET: UNKNOWN

DNA Duplex Target

```
     -618                        -590
5'-TCCTGCGCCTTGCTCCTTTGGTTCGTTCT-3'
3'-AGGACGCGGAACGAGGAAACCAAGCAAGA-5'
```

PARALLEL SYNTHETIC OLIGONUCLEOTIDE SEQUENCE

3'-TGGTGGGGGTTGGTGGTTTGGTTGGTTGT-5'  (APP2par)

ANTI-PARALLEL SYNTHETIC OLIGONUCLEOTIDE SEQUENCE

5'-TGGTGGGGGTTGGTGGTTTGGTTGGTTGT-3'  (APP2anti)

C. TARGET: UNKNOWN

DNA Duplex Target

```
     -477                                  -440
5'-TTCTCATTCTCTTCCAGAAACGCCTGCCCCACCTCTCC-3'
3'-AAGAGTAAGAGAAGGTCTTTGCGGACGGGGTGGATAGG-5'
```

PARALLEL SYNTHETIC OLIGONUCLEOTIDE SEQUENCE

3'-TTGTGTTTGTGTTGGTGTTTGGGGTGGGGGTGGTGTGG-5'  (APP3par)

ANTI-PARALLEL SYNTHETIC OLIGONUCLEOTIDE SEQUENCE

5'-TTGTGTTTGTGTTGGTGTTTGGGGTGGGGGTGGTGTGG-3'  (APP3anti)

D. TARGET: UNKNOWN

DNA Duplex Target

```
     -434                       -407
5'-GAGAGAAAAAACGAAATGCGGATAAAAA-3'
3'-CTCTCTTTTTTGCTTTACGCCTATTTTT-5'
```

PARALLEL SYNTHETIC OLIGONUCLEOTIDE SEQUENCE

5'-GTGTGTTTTTTGGTTTTGGGGTTTTTTT-3'  (APP4par)

ANTI-PARALLEL SYNTHETIC OLIGONUCLEOTIDE SEQUENCE

3'-GTGTGTTTTTTGGTTTTGGGGTTTTTTT-5'  (APP4anti)

E. TARGET: UNKNOWN

DNA Duplex Target

```
      -286                                -252
5'-CTCACCTTTCCCTGATCCTGCACCGTCCCTCTCCT-3'
3'-GAGTGGAAAGGGACTAGGACGTGGCAGGGAGAGGA-5'
```

-continued

PARALLEL SYNTHETIC OLIGONUCLEOTIDE SEQUENCE

3'-GTGTGGTTTGGGTGTTGGTGGTGGGTGGGTGTGGT-5' (APP5par)

ANTI-PARALLEL SYNTHETIC OLIGONUCLEOTIDE SEQUENCE

5'-GTGTGGTTTGGGTGTTGGTGGTGGGTGGGTGTGGT-3' (APP5anti)

F. TARGET: UNKNOWN

DNA Duplex Target

```
   -264                              -230
5'-CCGTCCCTCTCCTGGCCCCAGACTCTCCCTCCC-3'
3'-GGCAGGGAGAGGACCGGGGTCTGAGAGGGAGGG-5'
```

PARALLEL SYNTHETIC OLIGONUCLEOTIDE SEQUENCE

3'-GGGTGGGTGTGGTGGGGGGTGTGTGTGGGTGGG-5' (APP6par)

ANTI-PARALLEL SYNTHETIC OLIGONUCLEOTIDE SEQUENCE

5'-GGGTGGGTGTGGTGGGGGGTGTGTGTGGGTGGG-3' (APP6anti)

G. TARGET: UNKNOWN

DNA Duplex Target

```
   -200                -177
5'-GGGGAGCGGAGGGGGCGCGTGGGG-3'
3'-CCCCTCGCCTCCCCCGCGCACCCC-5'
```

PARALLEL SYNTHETIC OLIGONUCLEOTIDE SEQUENCE

5'-GGGGTGGGGTGGGGGGGGGTGGGG-3' (APP7par)

ANTI-PARALLEL SYNTHETIC OLIGONUCLEOTIDE SEQUENCE

3'-GGGGTGGGGTGGGGGGGGGTGGGG-5' (APP7anti)

H. TARGET: UNKNOWN

DNA Duplex Target

```
   -40                                  -9
5'-CTCGCCTGGCTCTGAGCCCCGCCGCCGCGCTC-3'
3'-GAGCGGACCGAGACTCGGGGCGGCGGCGCGAG-5'
```

PARALLEL SYNTHETIC OLIGONUCLEOTIDE SEQUENCE

3'-GTGGGGTGGGTGTGTGGGGGGGGGGGGGGGTG-5' (APP8par)

ANTI-PARALLEL SYNTHETIC OLIGONUCLEOTIDE SEQUENCE

5'-GTGGGGTGGGTGTGTGGGGGGGGGGGGGGGTG-3' (APP8anti)

EXAMPLE 7
The EGFR Promoter Domain

Inappropriately high expression of the epidermal growth factor gene (EGFR) has been implicated as crucial to the development of cancers and several skin diseases (psoriasis). The synthetic oligonucleotides described below were designed to selectively repress the expression of the EFGR gene in such diseases.

A. TARGET: SP1 BINDING SITE

DNA Duplex Target

```
   -109                       -83
5'-TCCGCCGAGTCCCCGCCTCGCCGCC-3'
3'-AGGCGGCTCAGGGGCGGAGCGGCGG-5'
```

PARALLEL SYNTHETIC OLIGONUCLEOTIDE SEQUENCE

3'-TGGGGGGTGTGGGGGGGTGGGGGGG-5' (EGFR1par)

ANTI-PARALLEL SYNTHETIC OLIGONUCLEOTIDE SEQUENCE

5'-TGGGGGGTGTGGGGGGGTGGGGGGG-3' (EGFR1anti)

B. TARGET SP1 BINDING SITE

DNA Duplex Target

```
   -307                         -281
5'-TCCCTCCTCCTCCCGCCCTGCCTCCC-3'
3'-AGGGAGGAGGAGGGCGGGACGGAGGG-5'
```

PARALLEL SYNTHETIC OLIGONUCLEOTIDE SEQUENCE

3'-TGGGTGGTGGTGGGGGGGTGGGTGGG-5' (EGFR2par)

ANTI-PARALLEL SYNTHETIC OLIGONUCLEOTIDE SEQUENCE

5'-TGGGTGGTGGTGGGGGGGTGGGTGGG-3'  (EGFR2anti)

C. TARGET SP1 BINDING SITE

DNA Duplex Target

```
  -352                                    -317
5'-TTCTCCTCCTCCTCTGCTCCTCCCGATCCCTCCTCC-3'
3'-AAGAGGAGGAGGAGACGAGGAGGGCTAGGGAGGAGG-5'
```

PARALLEL SYNTHETIC OLIGONUCLEOTIDE SEQUENCE

3'-TTGTGGTGGTGGTGTGGTGGTGGGGTTGGGTGGTGG-5'  (EGFR3par)

ANTI-PARALLEL SYNTHETIC OLIGONUCLEOTIDE SEQUENCE

5'-TTGTGGTGGTGGTGTGGTGGTGGGGTTGGGTGGTGG-3'  (EGFR3anti)

D. TARGET: NUCLEASE SENSITIVE DOMAIN REQUIRED FOR EGFR EXPRESSION

```
  -227                        -204
5'-GGGGACCTGGGAAAGAGGGAAAGG-3'
3'-CCCCTGGACCCTTTCTCCCTTTCC-5'
```

DNA Duplex Target

```
  -363                              -338
5'-TTCTCCTCCCTCCTCCTCGCATTCTCCTCCTCT-3'
3'-AAGAGGAGGGAGGAGGAGCGTAAGAGGAGGAGAGA-5'
```

PARALLEL SYNTHETIC OLIGONUCLEOTIDE SEQUENCE

3'-TTGTGGTGGGTGGTGGTGGGTGGGTGGTGGTGGTGT-5'  (EGFR4par)

ANTI-PARALLEL SYNTHETIC OLIGONUCLEOTIDE SEQUENCE

5'-TTGTGGTGGGTGGTGGTGGGTGGGTGGTGGTGGTGT-3'  (EGFR4anti)

EXAMPLE 8

The GSTpi GENE

Overexpression of the enzyme gluththione-s-transferase pi has been implicated as being responsible for the broad-range drug resistance which developes in a variety of cancers. The synthetic oligonucleotides described below are designed to repress GST-pi expression, thereby sensitizing cancerous tissue to traditional drug chemotherapy.

A. TARGET SITE: The target domain comprises the consensus binding sequences for the transcription activating factors AP1 and Sp1. Synthetic Oligonucleotides targeted against this will repress GSTpi transcription by means of competition with AP1 and Sp1.

DNA Duplex Target

```
  -68                             -39
5'-GACTCAGCACTGGGGCGGAGCGGGGCGGGA-3'
3'-CTGAGTCGTGACCCCGCCTCGCCCCGCCCT-5'
```

PARALLEL SYNTHETIC OLIGONUCLEOTIDE SEQUENCE

5'-GTGTGTGGTGTGGGGGGGTGGGGGGGGGGT-3'  (GST1par)

ANTI-PARALLEL SYNTHETIC OLIGONUCLEOTIDE SEQUENCE

3'-GTGTGTGGTGTGGGGGGGTGGGGGGGGGGT-5'  (GST1anti)

B. TARGET SITE: An enhancer-like polypurine sequence. A synthetic oligonucleotide targeted against this site will repress GSTps transcription by means of competition with the enhancer.

PARALLEL SYNTHETIC OLIGONUCLEOTIDE SEQUENCE

5'-GGGGTGGTGGGTTTGTGGGTTTGG-3'  (GST2par)

ANTI-PARALLEL SYNTHETIC OLIGONUCLEOTIDE SEQUENCE

3'-GGGGTGGTGGGTTTGTGGGTTTGG-5'  (GST2anti)

An unusual repetitive DNA segment. No function has been ascribed to this segment yet. However, it is within the control domain and may play a role in transcription initiation.

DNA Duplex Target

```
  -499                                      -410
5'-AAAATAAAATAAAATAAAATAAAATAAAAT-3'
3'-TTTTATTTTATTTTATTTTATTTTATTTTA-5'
```

-continued
PARALLEL SYNTHETIC OLIGONUCLEOTIDE SEQUENCE

5'-TTTTTTTTTTTTTTTTTTTTTTTTTTTTTTTT-3' (GST3par)

ANTI-PARALLEL SYNTHETIC OLIGONUCLEOTIDE SEQUENCE

3'-TTTTTTTTTTTTTTTTTTTTTTTTTTTTTTTT-5' (GST3anti)

EXAMPLE 9

The HMGCoA REDUCTASE GENE

HMGCoA Reductase is the enzyme which defines the rate limiting step in cholesterol biosynthesis. Its molecular genetics has been studied to understand the control of cholesterol synthesis. The described synthetic oligonucleotides will intervene in the program of cholesterol synthesis by means of modulating the transcription of HMGCoA.

A. TARGET SITE: The target is binding site for a repressor protein that appears to mediate end-product inhibition of transcription by cholesterol. The synthetic oligonucleotide is a synthetic repressor of HMGCoA expression, as an agonist of the cellular repressor.

DNA Duplex Target

```
    -167                              -135
5'-GGTGAGAGATGGTGCGGTGCCCGTTCTCCGCCC-3'
3'-CCACTCTCTACCACGCCACGGGCAAGAGGCGGG-5'
```

PARALLEL SYNTHETIC OLIGONUCLEOTIDE SEQUENCE

3'-GGTGTGTGTTGGTGGGGTGGGGGTTGTGGGGGG-5' (HMGCOA1par)

ANTI-PARALLEL SYNTHETIC OLIGONUCLEOTIDE SEQUENCE

5'-GGTGTGTGTTGGTGGGGTGGGGGTTGTGGGGGG-3' (HMGCOA1anti)

B. TARGET SITE: The target is a binding site for protein that appears to activate transcription of HMGCoA. The synthetic oligonucelotide against this site is a synthetic repressor of HMGCoA expression, as an antagonist of the cellular protein which binds to the target.

DNA Duplex Target

```
    -134                           -104
5'-GGGTGCGAGCAGTGGGCGGTTGTTAAGGCGA-3'
3'-CCCACGCTCGTCACCCGCCAACAATTCCGCT-5'
```

PARALLEL SYNTHETIC OLIGONUCLEOTIDE SEQUENCE

5'-GGGTGGGTGGTGTGGGGGGTTGTTTTGGGGT-3' (HMGCOA2par)

ANTI-PARALLEL SYNTHETIC OLIGONUCLEOTIDE SEQUENCE

3'-GGGTGGGTGGTGTGGGGGGTTGTTTTGGGGT-5' (HMGCOA2anti)

C. TARGET SITE: The target is a binding site protein that appears to activiate transcription of HMGCoA by binding to the "TATA box" domain. A TFO against this site is designed to be a synthetic repressor of HMGCoA expression, as an antagonist of the cellular protein which binds to the TATA box target.

DNA Duplex Target

```
    -41                              -6
5'-AGGCGATCGGACGATCCTTTCTTATTGGCGGCCCT-3'
3'-TCCGCTAGCCTGCTAGGAAAGAATAACCGCCGGGA-5'
```

PARALLEL SYNTHETIC OLIGONUCLEOTIDE SEQUENCE

3'-TGGGGTTGGGTGGTTGGTTTGTTTTTGGGGGGGGT-5' (HMGCOA3par)

ANTI-PARALLEL SYNTHETIC OLIGONUCLEOTIDE SEQUENCE

5'-TGGGGTTGGGTGGTTGGTTTGTTTTTGGGGGGGGT-3' (HMGCOA3anti)

EXAMPLE 10

Nerve Growth Receptor (NGFR)

The NGFR gene encodes a cell surface receptor required for nerve cell proliferation. It is overexpressed in neuroblastoma and melanomas. Triplex oligonucleotides are designed to repress the growth of those cancerous tissues. Activation of the gene would be a precondition of activation of nerve cell regeneration. The mRNA start site is at −122 in this number scheme.

A. TARGET SITE: Consensus Sp1 binding site

DNA Duplex Target

-continued

```
   -323                             -290
5'-GGGAACTGGGTACCAGGGCGGGATGGGTGAGAGG-3'
3'-CCCTTGACCCATGGTCCCGCCCTACCCACTCTCC-5'
```

PARALLEL SYNTHETIC OLIGONUCLEOTIDE SEQUENCE

5'-GGGTTGTGGGTTGGTGGGGGGGTTGGGTGTGTGG-3'  (NGFR1par)

ANTI-PARALLEL SYNTHETIC OLIGONUCLEOTIDE SEQUENCE

3'-GGGTTGTGGGTTGGTGGGGGGGTTGGGTGTGTGG-5'  NGFR1ap

B. TARGET SITE: Consensus Sp1 binding site

DNA Duplex Target

```
   -309                                 -275
5'-AGGGCGGGATGGGTGAGAGGCTCTAAGGGACAAGG-3'
3'-TCCCGCCCTACCCACTCTCCGAGATTCCCTGTTCC-5'
```

PARALLEL SYNTHETIC OLIGNUCLEOTIDE SEQUENCE

5'-TGGGGGGGTTGGGTGTGTGGGTGTTTGGGTGTTGG-3'  (NGFR2par)

ANTI-PARALLEL SYNTHETIC OLIGNUCLEOTIDE SEQUENCE

3'-TGGGGGGGTTGGGTGTGTGGGTGTTTGGGTGTTGG-5'  (NGFR2anti)

C. TARGET SITE: Domain flanking consensus Sp1 binding sites

DNA Duplex Target

```
   -285                                    -248
5'-AAGGGACAAGGCAGGGAGAAGCGCACGGGTGCGGGAA-3'
3'-TTCCCTGTTCCGTCCCTCTTCGCGTGCCCACGCCCTT-5'
```

PARALLEL SYNTHETIC OLIGONUCLEOTIDE SEQUENCE

5'-TTGGGTGTTGGGTGGGTGTTGGGGTGGGGTGGGGGTT-3'
(NGFR3par)

ANTI-PARALLEL SYNTHETIC OLIGONUCLEOTIDE SEQUENCE

3'-TTGGGTGTTGGGTGGGTGTTGGGGTGGGGTGGGGGTT-5'
(NGFR3anti)

D. TARGET SITE: Domain flanking consensus Sp1 binding sites

DNA Duplex Target

```
   -243                         -216
5'-CCCTCCCTTTGCCTCTGCTTCCCACCCC-3'
3'-GGGAGGGAAACGGAGACGAAGGGTGGGG-5'
```

PARALLEL SYNTHETIC OLIGONUCLEOTIDE SEQUENCE

5'-GGGTGGGTTTGGGTGTGGTTGGGTGGGG-3' (NGFR4par)

ANTI-PARALLEL SYNTHETIC OLIGONUCLEOTIDE SEQUENCE

3'-GGGTGGGTTTGGGTGTGGTTGGGTGGGG-5' (NGFR4anti)

TARGET SITE: Consensus Sp1 binding site.

DNA Duplex Target

```
   -187                                 -154
5'-GGGGGTGGGCGGGCTGGCGGGGCGGAGGCGGGGG-3'
3'-CCCCCACCCGCCCGACCGCCCCGCCTCCGCCCCC-5'
```

PARALLEL SYNTHETIC OLIGONUCLEOTIDE SEQUENCE

5'-GGGGGTGGGGGGGGTGGGGGGGGGGTGGGGGGGG-3'
(NGFR5par)

ANTI-PARALLEL SYNTHETIC OLIGONUCLEOTIDE SEQUENCE

3'-GGGGGTGGGGGGGTGGGGGGGGGGTGGGGGGGGG-5'
(NGFR5anti)

EXAMPLE 11
HERPEX SIMPLEX VIRUS 1: DNA Polymerase and DNA binding proteins

HSV-1 is responsible for a variety of skin lesions and other infections. The triplex oligonucleotide are designed to bind directly to the promotor region of the genes which encode the viral DNA polymerase and DNA binding protein, thereby arresting viral replication. Both genes occur at 0.4 map units and flank the replication origin oriL. Numbering below is in terms of the polypeptide start site for each gene.

A. TARGET SITE: This site is in the 5' flanking sequence of the DNA polymerase gene. The Angelotti strain has three base changes relative to strain 17.

(1) Strain 17

DNA Duplex Target

```
     -60                                    -26
5'-TTTTTCTCTTCCCCCCCTCCCCACATTCCCCTCTTT-3'
3'-AAAAAGAGAAGGGGGGAGGGGTGTAAGGGGAGAAA-5'
```

PARALLEL SYNTHETIC OLIGONUCLEOTIDE SEQUENCE

3'-TTTTTGTGTTGGGGGGGTGGGGTGTGGGGGGTGTTT-5'
(HSVPOL17par)

ANTI-PARALLEL SYNTHETIC OLIGONUCLEOTIDE SEQUENCE

5'-TTTTTGTGTTGGGGGGGTGGGGTGTGGGGGGTGTTT-3'
(HSVPOL17anti)

(2) Strain Angelotti

```
     -62                                      -26
5'-TTTTTCTCTTCCCCCCCTCCCCACATCCCCCCTCTTT-3'
3'-AAAAAGAGAAGGGGGGGAGGGGTGTAGGGGGGAGAAA-5'
```

PARALLEL SYNTHETIC OLIGONUCLEOTIDE SEQUENCE

3'-TTTTTGTGTTGGGGGGGTGGGGTGTTGGGGGGTGTTT-5'
(HSVPOL1par)

ANTI-PARALLEL SYNTHETIC OLIGONUCLEOTIDE SEQUENCE

5--TTTTTGTGTTGGGGGGGTGGGGTGTTGGGGGGTGTTT-3'
(HSVPOL1anti)

A. TARGET SITE: This site is in the 5' flanking sequence of the DNA binding protein gene for strain 17.

```
       -82                               -118
5'-AAAATCCGGGGGGGGGCGGCGACGGTCAAGGGGAGGG-3'

3'-TTTTAGGCCCCCCCCCGCCGCTGCCAGTTCCCCTCCC-5'
```

PARALLEL SYNTHETIC OLIGONUCLEOTIDE SEQUENCE

5'-TTTTTGGGGGGGGGGGGGGGGTGGGTGTTGGGGTGGG-3'
(HSVPOL2par)

ANTI-PARALLEL SYNTHETIC OLIGONUCLEOTIDE SEQUENCE

3'-TTTTTGGGGGGGGGGGGGGGGTGGGTGTTGGGGTGGG-5'
(HSVPOL2anti)

EXAMPLE 12
HERPES SIMPLEX VIRUS 1: origin of replication

HSV-1 is responsible for a variety of skin lesions and other infections. The triplex oligonucleotides are designed to bind directly to the two classes of HSV-1 DNA replication origin, thereby arresting viral replication. The first origin (oriL) occurs at 0.4 map units and is in between and immediately adjacent to the HSV-1 DNA polymerase and DNA binding protein genes. The two identical origins of the second type (oriS) occur at 0.82 and 0.97 map units. Numbering below is the terms of position relative to the two fold symmetry axis of each origin.

A. TARGET SITE oriL origin

1. DNA Duplex Target

−48                                                           −10
5'-AGGACAAAGTGCGAACGCTTCGCGTTCTCACTTTTTTT-3'

3'-TTTTTTTCACTCTTGCGCTTCGCAAGCGTGAAACAGGA-5'

PARALLEL SYNTHETIC OLIGONUCLEOTIDE SEQUENCE

5'-TTTTTTTGTGTGTTGGGGTTGGGTTGGGTGTTTGTGGT-3'
(HSVORL1par)

ANTI-PARALLEL SYNTHETIC OLIGONUCLEOTIDE SEQUENCE

3'-TTTTTTTGTGTGTTGGGGTTGGGTTGGGTGTTTGTGGT-5'
(HSVORL1anti)

2. DNA Duplex Target 10                                                           47
5'-AGGACAAAGTGCGAACGCTTCGCGTTCTCACTTTTTTT-3'

3'-TCCTCTTTCTCGCTTGCGAAGCGCAAGAGTGAAAAAAA-5'

PARALLEL SYNTHETIC OLIGONUCLEOTIDE SEQUENCE

3'-TGGTGTTTGTGGGTTGGGTTGGGGTTGTGTGTTTTTTT-5'
(HSVORL2par)

ANTI-PARALLEL SYNTHETIC OLIGONUCLEOTIDE SEQUENCE

5'-TGGTGTTTGTGGGTTGGGTTGGGGTTGTGTGTTTTTTT-3'
(HSVORL2anti)

These two targets sites are within the oriL origin. Because the oriL also comprises the 5' flanking domain of the HSV-1DNA polymerase and the HSV-1 major DNA binding protein, these triplex oligonucleotides may also interfere with transctiption of those two genes.

B. TARGET SITE: oriS organ

DNA Duplex Target

69                                                           −34
5'-AAGGGGGCGGGGCCGCCGGGTAAAAGAAGTGAGAA-3'

3'-TTCCCCCGCCCCGGCGGCCCATTTTCTTCACTCTT-5'

PARALLEL SYNTHETIC OLIGONUCLEOTIDE SEQUENCE

5'-TTGGGGGGGGGGGGGGGGGGTTTTTGTTGTGTGTT-3'
(HSVORS1par)

ANTI-PARALLEL SYNTHETIC OLIGONUCLEOTIDE SEQUENCE

3'-TTGGGGGGGGGGGGGGGGGGTTTTTGTTGTGTGTT-5'
(HSVORS1anti)

EXAMPLE 13

Human Beta Globin

The beta globin gene encodes one of the proteins comprising adult hemoglobin. Mutation in this gene is responsible for beta thalassemia and sickle cell anemia. Triplex oligonucleotides targeted to this gene are designed to inhibit the beta globin gene in thallassemics and in patients with sickle cell anemia, to be replaced by the naturally occurring delta protein. Two classes of triplex oligonucleotides TFO are described, which are targeted against the 5' enhancer or the promoter/coding domain. Numbering is relative to the principal mRNA start site.

A. DNA Duplex Target

−912                                                           −886
5'-CCTTTTCCCCTCCTACCCCTACTTTCT-3'

3'-GGAAAAGGGGAGGATGGGGATGAAAGA-5'

PARALLEL SYNTHETIC OLIGONUCLEOTIDE SEQUENCE

3'-GGTTTTGGGGTGGTTGGGGTTGTTTGT-5' (GL1par)

ANTI-PARALLEL SYNTHETIC OLIGONUCLEOTIDE SEQUENCE

5'-GGTTTTGGGGTGGTTGGGGTTGTTTGT-3' (GL1anti)

B. DNA Duplex Target

−63                                                           −25
5'-AGGAGCAGGGAGGGCAGGAGCCAGGGCTGGGCATAAAAG-3'

3'-TCCTCGTCCCTCCCGTCCTCGGTCCCCACCCGTATTTTC-5'

PARALLEL SYNTHETIC OLIGONUCLEOTIDE SEQUENCE

5'-TGGTGGTGGGTGGGGTGGTGGGTGGGGTGGGGTTTTTTG-3' (GL2par)

ANTI-PARALLEL SYNTHETIC OLIGONUCLEOTIDE SEQUENCE )

3'-TGGTGGTGGGTGGGGTGGTGGGTGGGGTGGGGTTTTTTG-5' (GL2anti

C. DNA Duplex Target

```
   -36                         -9
5'-AGGGCTGGGCATAAAAGTCAGGGCAGAG-3'

3'-TCCCGACCCGTATTTTCAGTCCCGTCTC-5'
```

PARALLEL SYNTHETIC OLIGONUCLEOTIDE SEQUENCE

5'-TGGGGTGGGGTTTTTTGTGTGGGGTGTG-3' (GL3par)

ANTI-PARALLEL SYNTHETIC OLIGONUCLEOTIDE SEQUENCE

3'-TGGGGTGGGGTTTTTTGTGTGGGGTGTG-5' (GL3anti)

D. DNA Duplex Target

```
   514                              543
5'-CCCTTGATGTTTTCTTTCCCCTTCTTTTCT-3'

3'-GGGAACTACAAAAGAAAGGGGAAGAAAAGA-5'
```

PARALLEL SYNTHETIC OLIGONUCLEOTIDE SEQUENCE

3'-GGGTTGTTGTTTTGTTTGGGGTTGTTTTGT-5' (GL4par)

ANTI-PARALLEL SYNTHETIC OLIGONUCLEOTIDE SEQUENCE

5'-GGGTTGTTGTTTTGTTTGGGGTTGTTTTGT-3' (GL4anti)

E. DNA Duplex Target

```
  693                         719
5'-TTCTTGCTTTCTTTTTTTTCTTCTCC-3'

3'-AAGAACGAAAGAAAAAAAAGAAGAGG-5'
```

PARALLEL SYNTHETIC OLIGONUCLEOTIDE SEQUENCE

3'-TTGTTGGTTTGTTTTTTTTGTTGTGG-5' (GL5par)

ANTI-PARALLEL SYNTHETIC OLIGONUCLEOTIDE SEQUENCE

5'-TTGTTGGTTTGTTTTTTTTGTTGTGG-3' (GL5anti)

F. DNA Duplex Target

```
  874                         900
5'-CTCCCTACTTTATTTTCTTTTATTTTT-3'

3'-GAGGGATGAAATAAAAGAAAATAAAAA-5'
```

PARALLEL SYNTHETIC OLIGONUCLEOTIDE SEQUENCE

3'-GTGGGTTGTTTTTTTTGTTTTTTTTTT-5' (GL5par)

ANTI-PARALLEL SYNTHETIC OLIGONUCLEOTIDE SEQUENCE

5'-GTGGGTTGTTTTTTTTGTTTTTTTTTT-3' (GL6anti)

EXAMPLE 14

Testing for the effect of oligonucleotide binding in cells. The effects of triplex-forming oligonucleotides are studied in cell culture. Oligonucleotides are administrered to cultured human cell lines, which are then analyzed for oligonucleotide uptake and for a change in the steady-state level of messenger RNA associated with the DNA target. As an example, the methods for the c-myc gene are shown. One skilled in the art will readily be able to generalize to any gene within a cultured cell.

HeLa cells grown on a solid support (100 ul total volume), are treated with $^{32}$P-labelled oligonucleotide, then incubated as a function of time and concentration. Cells are separated from serum by centrifugation and exhaustive washing, are disrupted by deproteinization then assayed quantitatively on a 8% sequencing gel. This analysis procedure yields the following characteristics:

a. The apparent partition coefficient for oligonucleotide uptake into HeLa cells.

b. The uptake rate, i.e., the time constant to reach a steady state with respect to oligonucleotide uptake.

c. The half-time for oligonucleotide degradation in serum and in the HeLa cell.

From those data, the optimized timecourse and titration range for the oligonucleotide teatment of cells is determined.

Transcription inhibition is assayed by a variation of the RNase protection assay, which is the standard assay for quantitying steady state mRNA levels in mammalian cells. Total cellular RNA is extrated from oligonucleotide-treated HeLa cells, then hybridized to a uniformly labelled antisense RNA transcript, generated by the action of T7 polymerase on the SmaI-PvuII human c-myc frangment in pSPT19.

This SmaI-PvuII probe is complementary to the first myc exon and sequences which comprise both the P1 and P2 transcription start sites of myc. When the probe is hybridized in excess over myc transcript, a limit RNaseI digest produces either a 0.6 kb duplex (transcription from P1, which is the preferred origin in HeLa cells) or a 0.4 kb duplex (transcription occurs instead from P2, which is used in HeLa cells under conditions of serum starvation).

The size and quantity of the resulting RNase resistant duplexes is then determined by quantitative autoradiography on a 5% acrylamide gel matrix. This assay system can quantify steady-state RNA levels to within 20% accuracy, which is sufficient for the purposes of this analysis.

The outcome of these cellular titrations is analyzed in the context of two control experiments. The first is a comparison of the dose response of oligonucleotides which bind selectively to the target gene and the dose response of oligonucleotides which are unrelated. If oligonucleotide-mediated repression of the c-myc transcription is due to site-specific triplex formation in the cell, then an unrelated oligonucleotide will not elicit an affect, over an equivalent concentration range.

The second control addresses the gene specificity of the effect. In the RNase protection assay, data are always normalized to overall RNA concentation in the cell. As such, changes in the steady state level of the myc transcript are meaningful in their own right. However to confirm that the effects of oligonucleotide binding are specific to the c-myc gene we also assay for the effect of myc-specific oligonucleotide treatment on the steady state levels of the histone 2A (H2A) message in HeLa cells, probing the RNA complement with an H2A antisense RNA, generated from a construct which, as for myc sequences, has been cloned into a RNA expression vector. When oligonucleotide mediated repression is specific to the myc gene, H2A transcription in HeLa cells will be unaffected, over an equivalent concentration range.

Over the 1 to 50 micro-molar range, oligonucleotides which bind to the control region of the human c-myc gene selectively repress c-myc transcription in an intact HeLa cell. Preliminary work with other oligonucleotides described in the examples have begun to display similar selectivity.

One skilled in the art will recognize that application of these methods is readily generalized to any gene in any cell line and is limited only by the availability of cloned gene constructs, DNA sequence data, and a rudimentary understandinng of the molecular genetics of the gene under investigation. At present, that battery of information is availale for several hundred human genes, and for several thousand genes from other species.

The methods can also be applied, without significant modification to the use of chemically altered oligonucleotides variants, such as those with chemical moieties added to the 3' nd 5' terminus, oligonucleotides with an altered phosphodiester backbone or those with bases other than G and T (i.e., iodo-G or X).

Ultimately, the importance of these examples is to show that a whole class of single strand oligonucleotide molecules are readily taken up by eukaryotic cells, without exogenous manipulation of any kind. The uptake mechanism is not known at present, but in most cells, it is efficient and, apparently, independent of oligonucleotide sequence (Eppstein D. A., Schryver B. B. & Marsh Y. V. (1986) J. Biol.Chem. 261, 5999) Therefore, in the most general sense, the overall uptake properties of such oligonucleotides are not significantly different from other potent drugs. By this criterion, it is certain that an oligonucleotide ligand designed to selectively intervene into the process of gene expression will show pharmacological effects in an intact cell.

In the past, these cell uptake concepts have been used to explain the effectiveness of RNA oligonucleotides as drugs which enhance the effect of interferon treatment (Eppstein D. A., Schryver B. B. & Marsh Y. V. (1986) J. Biol.Chem. 261, 5999) and of the ability of "antisense" or "anti-splice junction" oligonucleotides to selectively inhibit mRNA processing in the cell (Heikkile R. et. al. (1987) Nature 328, 445 and Eppstein D. A., Schryver B. B. & Marsh Y. V. (1986) J. Biol. Chem. 261, 5999). It is likely that the same uptake process is the basis for the use of triplex-forming oligonucleotides as drugs to selectively regulate transcription initiation or to selectively destroy a gene target.

The design process described herein can be used to design a synthetic DNA oligonucleotide which will bind specifically to any double strand DNA target of interest. The resulting oligonucleotide-duplex DNA complex is best described as a colinear triplex. In the triplex the oligonucleotide molecule occupies the major groove of the duplex. The complex is stabilized by base-base hydrogen bonding at the surface of the major groove, leaving Watson-Crick pairing intact. As a result, the stability and site specificity of the synthetic oligonucleotide is not significantly affected by modification of the phosphodiester linkage or by chemical modification of the oligonucleotide terminus. Consequently, these oligonucleotides can be chemically modified; enhancing the overall binding stability, increasing the stability with respect to chemical degradation, increasing the rate at which the oligonucleotides are transported into cells, and conferring chemical reactivity to the molecules.

Based upon the design method described herein, it is possible to design oligonucleotides which are readily taken up by eukaryotic cells and, once in the cell, can be targeted to specific sites within a genome. Currently, the site specificity and stability of the synthetic oligonucleotide-target site interaction is as good as current monoclonal antibody-antigen binding interactions.

This new class of site specific molecules can be used as gene-specific reagents with the capacity to control the transcription process in a gene-specific fashion. This control is effective on both somatic genes and viral genes which have infected a host cell. When synthetic oligonucleotides are appropriately coupled to a reactive chemical complement, it is possible to create a hybrid molecule with the capacity to selectively destroy a gene target of interest.

One skilled in the art will readily appreciate that the present invention is well adapted to carry out the objects and attain the ends and advantages mentioned as well as those inherent therein. The oligonucleotides, compounds, methods, procedures and techniques described herein are presently representative of preferred embodiments, are intended to be exemplary, and are not intended as limitations on the scope. Changes therein and other uses will occur to those skilled in the art which are encompassed within the spirit of the invention or defined by the scope of the appended claims.

What is claimed is:

1. A method of making a synthetic oligonucleotide which binds to a target sequence in duplex DNA forming a collinear triplex by binding to the major groove, said method comprising the steps of:
 (a) identifying a duplex nucleotide target sequence of greater than about 20 nucleotides on each strand, said target sequence having either about at least 65% purine bases or about at least 65% pyrimidine bases on each strand; and
 (b) synthesizing said synthetic olignucleotide complementary to said identified target sequence, said synthetic oligonucleotide including a G and a T, wherein said synthetic oligonucleotide has a G when the complementary location in the DNA duplex has a GC base pair and has a T when the complementary location in the DNA duplex has an AT base pair.

2. The method of claim 1 wherein said synthetic oligonucleotide is oriented 3' to 5' and binds anti-parallel to the about at least 65% purine strand, wherein the orienting strand of the duplex DNA is the more purine rich strand.

3. The method of claim 1, wherein said synthetic oligonucleotide is oriented 5' to 3' and binds parallel to the about at least 65% purine strand, wherein the orienting strand of the duplex DNA is the more purine rich strand.

* * * * *

UNITED STATES PATENT AND TRADEMARK OFFICE
CERTIFICATE OF CORRECTION

PATENT NO. : 5,176,996
DATED : January 5, 1993
INVENTOR(S) : Michael E. Hogan, et al Page 1 of 2

It is certified that error appears in the above-indentified patent and that said Letters Patent is hereby corrected as shown below:

Column 4, line 63, change "FIGS. 4A-4D" to -- FIGS. 4A-4H --.

Column 5, line 39, before "fragment" change "env" to -- env --.

Column 5, line 56, after "HIV-1" change "env" to -- env --.

Column 5, line 58, after "ratio of" change "env" to -- env --.

Column 6, lines 19-20, change "thymine as refers" to -- thymine, U refers --.

Column 7, lines 4-17, delete blank lines.

Column 8, line 45, after "spermine" change "PH" to -- pH --.

Column 18, line 59, change "T-5'" to -- -5' --.

Column 19, line 23, change "in vitro" to -- in vitro --.

Column 19, line 27, change "in vitro" to -- in vitro --.

Column 19, line 29, change "env" to -- env --.

Column 19, line 47, change "tar" to -- tar --.

Column 19, line 55, change "tar" to -- tar --.

UNITED STATES PATENT AND TRADEMARK OFFICE
CERTIFICATE OF CORRECTION

PATENT NO. : 5,176,996
DATED : January 5, 1993
INVENTOR(S) : Michael E. Hogan, et al It is certified that error appears in the above-indentified patent and that said Letters Patent is hereby corrected as shown below:

Column 22, line 8, change "(APPIpar)" to -- (APP1par) --.

Column 22, line 10, change "(APPIanti)" to -- (APP1anti) --.

Column 25, line 67, change "GSTps" to -- GSTpi --.

Signed and Sealed this

Twenty-fifth Day of April, 1995

BRUCE LEHMAN

Attest:

Attesting Officer

Commissioner of Patents and Trademarks